(12) United States Patent
Lee et al.

(10) Patent No.: US 9,695,279 B2
(45) Date of Patent: Jul. 4, 2017

(54) POLYMER FOR PREPARING RESIST UNDERLAYER FILM, RESIST UNDERLAYER FILM COMPOSITION CONTAINING THE POLYMER AND METHOD FOR FORMING RESIST UNDERLAYER FILM USING THE COMPOSITION

(71) Applicants: SK Innovation Co., Ltd., Seoul (KR); SK Global Chemical Co., Ltd., Seoul (KR)

(72) Inventors: Kwang Kuk Lee, Daejeon (KR); Jin Su Ham, Daejeon (KR); Sun Joo Kim, Daejeon (KR); Hye Ryoung Lee, Daejeon (KR); Min Ho Jung, Daejeon (KR)

(73) Assignees: SK Innovation Co., Ltd., Seoul (KR); SK Global Chemical Co., Ltd., Seoul (KR)

( * ) Notice: Subject to any disclaimer, the term of this patent is extended or adjusted under 35 U.S.C. 154(b) by 0 days.

(21) Appl. No.: 15/133,808

(22) Filed: Apr. 20, 2016

(65) Prior Publication Data

US 2016/0311975 A1 Oct. 27, 2016

(30) Foreign Application Priority Data

Apr. 22, 2015 (KR) ........................ 10-2015-0056831

(51) Int. Cl.
| | | |
|---|---|---|
| C08G 65/38 | (2006.01) | |
| C07C 323/18 | (2006.01) | |
| C07C 39/17 | (2006.01) | |
| C07C 39/42 | (2006.01) | |
| C07C 43/225 | (2006.01) | |
| C07C 43/23 | (2006.01) | |
| C09D 171/00 | (2006.01) | |
| G03F 7/11 | (2006.01) | |
| H01L 21/027 | (2006.01) | |
| G03F 7/09 | (2006.01) | |

(52) U.S. Cl.
CPC .............. *C08G 65/38* (2013.01); *C07C 39/17* (2013.01); *C07C 39/42* (2013.01); *C07C 43/225* (2013.01); *C07C 43/23* (2013.01); *C07C 323/18* (2013.01); *C09D 171/00* (2013.01); *G03F 7/094* (2013.01); *C07C 2103/18* (2013.01); *C07C 2103/40* (2013.01)

(58) Field of Classification Search
CPC ... C08G 65/38; H01L 21/0271; C07C 323/18; C07C 39/42; C07C 171/00; C07C 43/23; C07C 39/17; C07C 43/225; C07C 2103/40; C07C 2103/18; G03F 7/11
See application file for complete search history.

(56) References Cited

U.S. PATENT DOCUMENTS

| | | | | |
|---|---|---|---|---|
| 5,447,960 | A * | 9/1995 | Sinnott | A01N 31/08 514/297 |
| 6,329,492 | B1 * | 12/2001 | Sue | C07C 39/17 257/E23.119 |
| 2004/0135131 | A1 * | 7/2004 | Treacher | C07C 17/2632 252/582 |
| 2005/0075473 | A1 * | 4/2005 | Cella | C07C 29/40 528/86 |
| 2007/0275325 | A1 | 11/2007 | Hatakeyama et al. | |
| 2008/0153033 | A1 * | 6/2008 | Hyung | G03F 7/091 430/281.1 |
| 2016/0016872 | A1 * | 1/2016 | Aqad | C07C 39/17 430/313 |

FOREIGN PATENT DOCUMENTS

KR 1020140123368 A 10/2014

OTHER PUBLICATIONS

Burnell et al ,"Synthesis and Electrooptical Properties of Copolymers Derived from Phenol-Functionalized Telechelic Oligofluorenes", Macromolecules 2005, vol. 38, pp. 10667-10677.*

* cited by examiner

*Primary Examiner* — Cynthia Hamilton
(74) *Attorney, Agent, or Firm* — The Webb Law Firm

(57) ABSTRACT

Provided are a fluoreneol-based monomer, a polymer for preparing a resist underlayer film obtained therefrom, a resist underlayer film composition containing the polymer, and a method for forming a resist underlayer film using the resist underlayer film composition, wherein the fluoreneol-based monomer is represented by Chemical Formula 2 below:

[Chemical Formula 2]

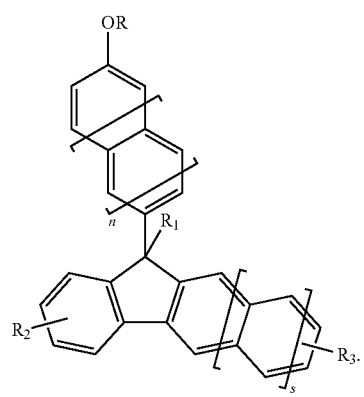

13 Claims, 1 Drawing Sheet

POLYMER FOR PREPARING RESIST UNDERLAYER FILM, RESIST UNDERLAYER FILM COMPOSITION CONTAINING THE POLYMER AND METHOD FOR FORMING RESIST UNDERLAYER FILM USING THE COMPOSITION

CROSS-REFERENCE TO RELATED APPLICATION

This application claims priority to Korean Patent Application No. 10-2015-0056831 filed Apr. 22, 2015, the disclosure of which is hereby incorporated in its entirety by reference.

TECHNICAL FIELD

The following disclosure relates to a novel fluoreneol-based monomer, a polymer for preparing a resist underlayer film obtained therefrom, a resist underlayer film composition containing the polymer, and a method for forming a resist underlayer film using the resist underlayer film composition.

BACKGROUND

As size of patterns is rapidly decreased in accordance with miniaturization and high integration of semiconductor devices, a collapse phenomenon of photoresist patterns has emerged as the hardest part during processes, and accordingly, it is inevitable that a thickness of a photoresist film and patterns becomes gradually thinner to achieve a high resolution image. However, since it is difficult to etch a material layer to be etched by using patterns formed with a thinner photoresist, an inorganic or organic film having strong etching resistance is introduced between the material layer and the photoresist. This inorganic or organic film refers to an underlayer film or a hardmask, and a hard mask process refers to a general process of etching the hard mask using the photoresist patterns to perform patterning, and etching the material layer using the patterns of the hard mask. Inorganic underlayer film used for the hard mask process is made of polysilicon, silicon nitride, silicon oxynitride, titanium nitride, amorphous carbon, etc., and is conventionally formed by chemical vapor deposition (CVD).

The hard mask formed by the chemical vapor deposition has good physical properties in view of etching selectivity or etching resistance, but has problems such as particle occurrence, void occurrence in a part having large steps, etc., particularly, high investment cost for initial equipments. In order to solve these problems, a need for developing a spin-on hard mask composition that is easily capable of performing spin-coating using a track system used in a photolithography process in a semiconductor line instead of using the deposited hard mask emerged, and development of specific materials for solving these problems has been attempted. The hard mask (spin-on hard mask) formed by the spin-coating has difficulty in obtaining the same etching resistance as the hard mask formed by CVD process. However, the hard mask formed by the spin-coating has advantages in that it is easier to form a thin film by a solution stage of coating, and coating uniformity and roughness of thin film surface are improved, etc. In addition, the initial investment cost of the hard mask formed by the spin-coating is less than that of the hard mask formed by a CVD process.

As described above, the recent trend of miniaturization of a lithography process according to continuous integration of LSI (large scale integrated circuit) has reached the limit for being implemented as an argon fluoride immersion lithography photoresist which is the top in the existing photoresist. In particular, in order to perform an ultrafine patterning process of 30 nm node or less, resolution of the photoresist used in the lithography process functions is an important factor. However, since the existing photoresist has a limitation in implementing patterns of 30 nm or less, development of a novel additional process has been attempted to overcome the limitation.

Technologies that are practically applied among a number of currently developed technologies are mainly a double patterning method in which primary and secondary exposure processes and an etching process are performed and a double patterning process (SPT, Spacer Patterning Technology) using a spacer, and materials used as a hard mask in the additional process commonly refer to an underlayer film composition. It is noted that in addition to the use of amorphous carbon as a hard mask, the used amount of the underlayer film composition has been rapidly increased as a novel hard mask material in a situation in which the double patterning process which is a process for implementing new high resolution generally leads ArF lithography process. The largest physical properties that are required for the underlayer film include high etching resistance, thermal stability, excellent solubility to general organic solvents, storage stability, adhesion property, and excellent coating uniformity, etc. The reason for requiring thermal stability is that an underlayer film is formed, and then, a vacuum deposition process at high temperature is performed on an upper part thereof as a subsequent process, wherein in view of heat resistance, low decomposition of a polymer at 400° C. and a film decrease by 5% or less are generally required for a stable vacuum deposition process. The etching resistance is another factor that is significantly important for etching a substrate while having the minimum thickness as the underlayer film. The reason is because as a thickness of the film is increased, risk that patterns may naturally collapse during the process is increased. The etching resistance is favorable as carbon content of a polymer is high, but it is preferred that the carbon content of the polymer is 82% or more in consideration of solubility to a solvent, coating uniformity, etc.

In the related art, polymers having high carbon content and polarity and high thermal stability have been mainly studied as a polymer material in a composition in order to satisfy characteristics of the underlayer film material, and in particular, polyamide, polyetheretherketone, polyaryl ether, other phenolic polymers, etc., have been variously studied. It was confirmed that some of the polymers had sufficient high-temperature stability and a film-forming ability. However, when polymers have desired level of carbon contents related with etching resistance, the polymers have problems in view of storage stability, line compatibility, and coating uniformity due to rapid decrease in solubility. When polymers have insufficient heat resistance, the polymers have a problem in that a gas emission amount is large during the process due to low thermal stability.

That is, physical properties of the underlayer film composition are dependent on characteristics of the polymer. In particular, thermal stability and etching resistance in the characteristics of the polymer are intactly reflected in the characteristics of the underlayer film composition. The thermal stability is dependent on stability of a polymer main chain, and the etching resistance is excellent as a carbon content present in the polymer is high. On the contrary, as the number of hetero elements such as oxygen or nitrogen is increased, the etching resistance is decreased. The thermal stability is dependent on a chemical structure and bond strength of the polymer. In particular, the number of compounds of which stability is maintained at a temperature of 400° C. or more is small. Examples of the polymer having excellent thermal stability may include polyimide, polyamide, polyarylketone ether, etc. However, the polymers having excellent thermal stability have limitation in being used as the underlayer film material since etching resistance is decreased or solubility with respect to general organic solvents is low.

In addition, surface planarization and uniformity of pattern edges may be controlled by a molecular weight of the polymer or an additive. Other mechanical properties of the pattern are also determined by kinds and structures of the polymer.

RELATED ART DOCUMENT (Patent Document 1) Korean Patent Laid-Open Publication No. KR 2014-0123368
(Patent Document 2) U.S. Patent Application Publication No. 2007-0275325A1

SUMMARY

The present inventors synthesized a novel fluorene-based polymer capable of improving etching resistance while having excellent thermal stability and coating uniformity to overcome the above-described problems, and found that the novel fluorene-based polymer had excellent thermal stability, etching resistance, and coating uniformity, and simultaneously had high solubility to organic solvents conventionally used in a semiconductor process even though the polymer had a high carbon content, thereby remarkably improving storage stability and line compatibility, and completed the present invention.

An embodiment of the present invention is directed to providing a polymer for preparing a resist underlayer film having excellent thermal stability, etching resistance, and coating uniformity.

Another embodiment of the present invention is directed to providing a resist underlayer film composition containing the polymer for preparing the resist underlayer film to thereby have excellent thermal stability, etching resistance, surface planarization, and gap-fill characteristic and superior mechanical properties of patterns.

Still another embodiment of the present invention is directed to providing a method for forming a resist underlayer film using the resist underlayer film composition.

Still another embodiment of the present invention is directed to providing a novel fluoreneol-based monomer for preparing the polymer for preparing the resist underlayer film.

In one general aspect, there is provided a polymer for preparing a resist underlayer film including: a repeating unit represented by Chemical Formula 1 below:

[Chemical Formula 1]

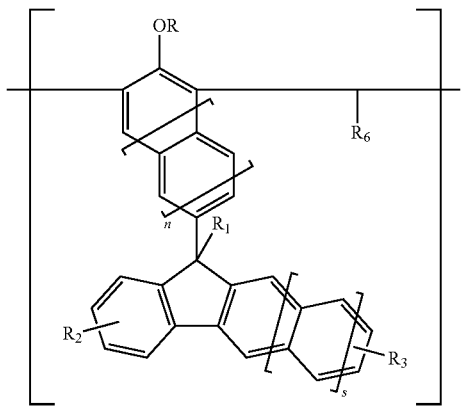

in Chemical Formula 1,
R is hydrogen, (C1-C10)alkyl, (C3-C10)cycloalkyl, (C6-C20)aryl, (C1-C10)alkyl(C6-C20)aryl or (C6-C20)aryl(C1-C10)alkyl;
$R_1$ is

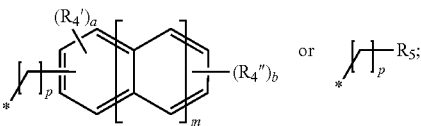

$R_4'$ and $R_4''$ are each independently hydrogen, (C1-C10)alkyl, (C3-C10)cycloalkyl, (C2-C10)alkenyl, (C3-C10)cycloalkenyl, (C2-C10)alkynyl, 4- to 10-membered heterocycloalkyl, (C6-C20)aryl, (C3-C20)heteroaryl, halogen, cyano, (C1-C10)alkoxy, (C3-C10)cycloalkoxy, (C6-C20)aryloxy, (C1-C10)alkylthio, (C3-C10)cycloalkylthio, (C6-C20)arylthio, (C1-C10)alkylcarbonyl, (C2-C10)alkenylcarbonyl, (C6-C20)arylcarbonyl, (C3-C10)cycloalkylcarbonyl, or (C3-C10)cycloalkenylcarbonyl;
$R_5$ is non-aromatic polycyclic (C4-C30)cycloalkyl;
$R_2$ and $R_3$ are each independently hydrogen, (C1-C10)alkyl, (C3-C10)cycloalkyl, (C2-C10)alkenyl, (C3-C10)cycloalkenyl, (C2-C10)alkynyl, 4- to 10-membered heterocycloalkyl, (C6-C20)aryl, (C3-C20)heteroaryl, halogen, cyano, (C1-C10)alkoxy, (C3-C10)cycloalkoxy, (C6-C20)aryloxy, (C1-C10)alkylthio, (C3-C10)cycloalkylthio, (C6-C20)arylthio, (C1-C10)alkylcarbonyl, (C2-C10)alkenylcarbonyl, (C6-C20)arylcarbonyl, (C3-C10)cycloalkylcarbonyl, or (C3-C10)cycloalkenylcarbonyl;
the alkyl, cycloalkyl, alkenyl, cycloalkenyl, alkynyl, heterocycloalkyl, aryl, heteroaryl, alkoxy, cycloalkoxy, aryloxy, alkylthio, cycloalkylthio, arylthio, alkylcarbonyl, alkenylcarbonyl, arylcarbonyl, cycloalkylcarbonyl, or cycloalkenylcarbonyl of $R_4'$, $R_4''$, $R_2$ and $R_3$ may be further substituted with one or more substituents selected from the group consisting of halogen, cyano, nitro, (C1-C10)alkyl, (C3-C10)cycloalkyl, (C6-C20)aryl, (C3-C20)heteroaryl, (C1-C10)alkoxy, (C6-C20)aryloxy, halo(C1-C10)alkyl and halo(C1-C10)alkoxy;
$R_6$ is hydrogen, (C1-C10)alkyl, (C3-C10)cycloalkyl or (C6-C20)aryl, and the alkyl, cycloalkyl, or aryl of $R_6$ may be further substituted with one or more substituents selected from the group consisting of (C1-C10)alkyl and (C6-C20)aryl;
a is an integer of 1 to 3, and when a is an integer of 2 or more, each $R_4'$ may be the same as each other or different from each other;
b is an integer of 1 or 2, and when b is an integer of 2, each $R_4''$ may be the same as each other or different from each other;
p is an integer of 0 to 7;
m is an integer of 0 to 4;
n is an integer of 0 to 4;
s is an integer of 0 to 4; and
the heteroaryl and the heterocycloalkyl include one or more heteroatoms selected from B, N, O, S, P(=O), Si, Se and P.

In addition, in another general aspect, there is provided a resist underlayer film composition containing the polymer for preparing the resist underlayer film including the repeating unit represented by Chemical Formula 1; and an organic solvent.

Further, in another general aspect, there is provided a method for forming a resist underlayer film including: forming a coating layer by spin-coating the resist underlayer film composition as described above on a wafer, the resist underlayer film composition including the polymer for preparing the resist underlayer film including the repeating unit represented by Chemical Formula 1; and the organic solvent; and forming a resist underlayer film by heating the wafer on which the coating layer is formed.

In addition, in another general aspect, there is provided a fluoreneol-based monomer represented by Chemical Formula 2 below:

[Chemical Formula 2]

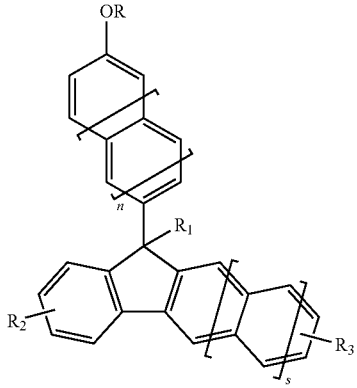

in Chemical Formula 2,

R is hydrogen, (C1-C10)alkyl, (C3-C10)cycloalkyl, (C6-C20)aryl, (C1-C10)alkyl(C6-C20)aryl or (C6-C20)aryl(C1-C10)alkyl;

$R_1$ is

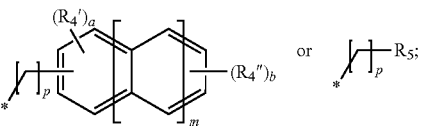

$R_4'$ and $R_4''$ are each independently hydrogen, (C1-C10)alkyl, (C3-C10)cycloalkyl, (C2-C10)alkenyl, (C3-C10)cycloalkenyl, (C2-C10)alkynyl, 4- to 10-membered heterocycloalkyl, (C6-C20)aryl, (C3-C20)heteroaryl, halogen, cyano, (C1-C10)alkoxy, (C3-C10)cycloalkoxy, (C6-C20)aryloxy, (C1-C10)alkylthio, (C3-C10)cycloalkylthio, (C6-C20)arylthio, (C1-C10)alkylcarbonyl, (C2-C10)alkenylcarbonyl, (C6-C20)arylcarbonyl, (C3-C10)cycloalkylcarbonyl, or (C3-C10)cycloalkenylcarbonyl;

$R_5$ is non-aromatic polycyclic (C4-C30)cycloalkyl;

$R_2$ and $R_3$ are each independently hydrogen, (C1-C10)alkyl, (C3-C10)cycloalkyl, (C2-C10)alkenyl, (C3-C10)cycloalkenyl, (C2-C10)alkynyl, 4- to 10-membered heterocycloalkyl, (C6-C20)aryl, (C3-C20)heteroaryl, halogen, cyano, (C1-C10)alkoxy, (C3-C10)cycloalkoxy, (C6-C20)aryloxy, (C1-C10)alkylthio, (C3-C10)cycloalkylthio, (C6-C20)arylthio, (C1-C10)alkylcarbonyl, (C2-C10)alkenylcarbonyl, (C6-C20)arylcarbonyl, (C3-C10)cycloalkylcarbonyl, or (C3-C10)cycloalkenylcarbonyl;

the alkyl, cycloalkyl, alkenyl, cycloalkenyl, alkynyl, heterocycloalkyl, aryl, heteroaryl, alkoxy, cycloalkoxy, aryloxy, alkylthio, cycloalkylthio, arylthio, alkylcarbonyl, alkenylcarbonyl, arylcarbonyl, cycloalkylcarbonyl, or cycloalkenylcarbonyl of $R_4'$, $R_4''$, $R_2$ and $R_3$ may be further substituted with one or more substituents selected from the group consisting of halogen, cyano, nitro, (C1-C10)alkyl, (C3-C10)cycloalkyl, (C6-C20)aryl, (C3-C20)heteroaryl, (C1-C10)alkoxy, (C6-C20)aryloxy, halo(C1-C10)alkyl and halo(C1-C10)alkoxy;

a is an integer of 1 to 3, and when a is an integer of 2 or more, each $R_4'$ may be the same as each other or different from each other;

b is an integer of 1 or 2, and when b is an integer of 2, each $R_4''$ may be the same as each other or different from each other;

p is an integer of 0 to 7;
m is an integer of 0 to 4;
n is an integer of 0 to 4;
s is an integer of 0 to 4; and
the heteroaryl and the heterocycloalkyl include one or more heteroatoms selected from B, N, O, S, P(=O), Si, Se and P.

DETAILED DESCRIPTION OF EMBODIMENTS

Figure 1:
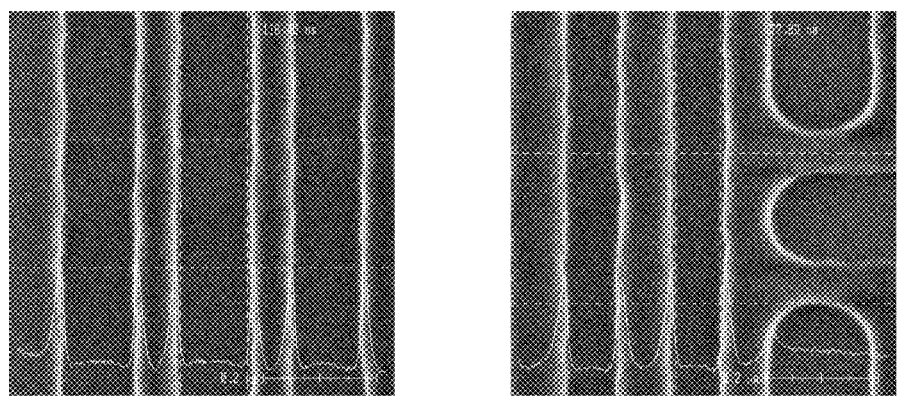
FIG. 1 shows mask CD point images after a photolithography process in evaluation 6 of Experimental Example 1.

Hereinafter, the present invention will be described in detail.

The present invention provides a core material for preparing a composition having excellent physical properties of an underlayer film used in a process for manufacturing a semiconductor and a display, and provides a polymer for preparing a resist underlayer film including a repeating unit represented by Chemical Formula 1 below:

[Chemical Formula 1]

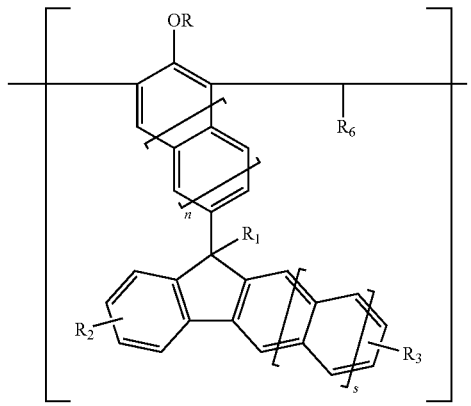

in Chemical Formula 1,

R is hydrogen, (C1-C10)alkyl, (C3-C10)cycloalkyl, (C6-C20)aryl, (C1-C10)alkyl(C6-C20)aryl or (C6-C20)aryl(C1-C10)alkyl;

$R_1$ is

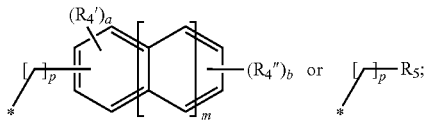

$R_4'$ and $R_4''$ are each independently hydrogen, (C1-C10) alkyl, (C3-C10)cycloalkyl, (C2-C10)alkenyl, (C3-C10)cycloalkenyl, (C2-C10)alkynyl, 4- to 10-membered heterocycloalkyl, (C6-C20)aryl, (C3-C20)heteroaryl, halogen, cyano, (C1-C10)alkoxy, (C3-C10)cycloalkoxy, (C6-C20) aryloxy, (C1-C10)alkylthio, (C3-C10)cycloalkylthio, (C6-C20)arylthio, (C1-C10)alkylcarbonyl, (C2-C10)alkenylcarbonyl, (C6-C20)arylcarbonyl, (C3-C10)cycloalkylcarbonyl, or (C3-C10)cycloalkenylcarbonyl;

$R_5$ is non-aromatic polycyclic (C4-C30)cycloalkyl;

$R_2$ and $R_3$ are each independently hydrogen, (C1-C10) alkyl, (C3-C10)cycloalkyl, (C2-C10)alkenyl, (C3-C10)cycloalkenyl, (C2-C10)alkynyl, 4- to 10-membered heterocycloalkyl, (C6-C20)aryl, (C3-C20)heteroaryl, halogen, cyano, (C1-C10)alkoxy, (C3-C10)cycloalkoxy, (C6-C20) aryloxy, (C1-C10)alkylthio, (C3-C10)cycloalkylthio, (C6-C20)arylthio, (C1-C10)alkylcarbonyl, (C2-C10)alkenylcarbonyl, (C6-C20)arylcarbonyl, (C3-C10)cycloalkylcarbonyl, or (C3-C10)cycloalkenylcarbonyl;

the alkyl, cycloalkyl, alkenyl, cycloalkenyl, alkynyl, heterocycloalkyl, aryl, heteroaryl, alkoxy, cycloalkoxy, aryloxy, alkylthio, cycloalkylthio, arylthio, alkylcarbonyl, alkenylcarbonyl, arylcarbonyl, cycloalkylcarbonyl, or cycloalkenylcarbonyl of $R_4'$, $R_4''$, $R_2$ and $R_3$ may be further substituted with one or more substituents selected from the group consisting of halogen, cyano, nitro, (C1-C10)alkyl, (C3-C10)cycloalkyl, (C6-C20)aryl, (C3-C20)heteroaryl, (C1-C10)alkoxy, (C6-C20)aryloxy, halo(C1-C10)alkyl and halo(C1-C10)alkoxy;

$R_6$ is hydrogen, (C1-C10)alkyl, (C3-C10)cycloalkyl or (C6-C20)aryl, and the alkyl, cycloalkyl, or aryl of $R_6$ may be further substituted with one or more substituents selected from the group consisting of (C1-C10)alkyl and (C6-C20) aryl;

a is an integer of 1 to 3, and when a is an integer of 2 or more, each $R_4'$ may be the same as each other or different from each other;

b is an integer of 1 or 2, and when b is an integer of 2, each $R_4''$ may be the same as each other or different from each other;

p is an integer of 0 to 7;
m is an integer of 0 to 4;
n is an integer of 0 to 4;
s is an integer of 0 to 4; and
the heteroaryl and the heterocycloalkyl include one or more heteroatoms selected from B, N, O, S, P(=O), Si, Se and P.

The polymer for preparing the resist underlayer film including the repeating unit represented by Chemical Formula 1 may have excellent etching resistance, thermal stability and coating uniformity, and may have excellent solubility to organic solvents even though the polymer has a high carbon content, thereby effectively forming the resist underlayer film by a spin-on coating method. In addition, when the resist underlayer film is formed on the substrate having predetermined patterns by the spin-on coating method, a gap-fill characteristic capable of filling a gap between the patterns and a planarization characteristic are also excellent. Further, the polymer for preparing the resist underlayer film including the repeating unit represented by Chemical Formula 1 may have excellent solubility to organic solvents, thereby improving storage stability.

Terms: ⌈alkyl⌋ and ⌈alkoxy⌋ described in the present invention include both a linear type or a branched type.

Term: ⌈aryl⌋ described in the present invention is an organic radical derived from aromatic hydrocarbon by removal of one hydrogen, and includes a single ring system or a fused ring system including 4 to 7 ring atoms, preferably, 5 or 6 ring atoms in each ring, and even includes a form in which a plurality of aryls are connected by a single bond. Specific examples of the aryl radical include aromatic groups such as phenyl, naphthyl, biphenyl, indenyl, fluorenyl, phenanthrenyl, anthracenyl, triphenylenyl, pyrenyl, crycenyl and naphthacenyl.

Term: ⌈heteroaryl⌋ described in the present invention means an aryl group containing 1 to 4 heteroatoms selected from B, N, O, S, P(=O), Si and P as an aromatic ring backbone atom and carbon as a remaining aromatic ring backbone atom, and may include 5- to 6-membered monocyclic heteroaryl and polycyclic heteroaryl condensed with at least one benzene ring, and may be partially saturated. In addition, heteroaryl in the present invention may also include a form in which one or more heteroaryls are connected by a single bond. Examples of the heteroaryl radical may include imidazolyl, oxazolyl, pyrazinyl, thiophenyl, quinolyl, benzofuryl, pyridiyl, indolyl, pyrrolyl, pyranyl, naphthyridinyl, etc., but the examples of the heteroaryl radical are not limited thereto.

Term: ⌈cycloalkyl⌋ described in the present invention means a monovalent alicyclic alkyl radical consisting of one ring. Examples of the cycloalkyl may include cyclopropyl, cyclobutyl, cyclopentyl, cyclohexyl, cycloheptyl, cyclooctyl, cyclononyl, cyclodecyl, etc., but examples of the cycloalkyl are not limited thereto.

Term: ⌈non-aromatic polycyclic cycloalkyl⌋ described in the present invention means a saturated or a partially unsaturated fused multicyclic radical, and specifically includes (C4-C30)bicycloalkyl, (C5-C30)tricycloalkyl, or (C6-C30) tetracycloalkyl.

Term: ⌈heterocycloalkyl⌋ described in the present invention means a completely saturated and partially unsaturated monocyclic or polycyclic hydrocarbon ring including one or more heteroatoms selected from N, O, S, P(=O), Si, Se and P in a ring as the heteroatom, wherein the number of heteroatoms is 1 to 4, and preferably, 1 to 2. Examples of the heterocycloalkyl radical may include morpholinyl, piperazinyl, piperidinyl, pyrrolidinyl, tetrahydropyranyl, thiomorpholinyl, etc., but the examples of the heterocycloalkyl radical are not limited thereto.

Term: ⌈Alkenyl⌋ described in the present invention means a linear or branched hydrocarbon radical containing at least one carbon-carbon double bond, and includes ethenyl, propenyl, butenyl, pentenyl, etc., but the examples of the alkenyl are not limited thereto.

Term: ⌈Alkynyl⌋ described in the present invention means a linear or branched hydrocarbon radical containing at least one carbon-carbon triple bond, and includes ethynyl, propynyl, butynyl, pentynyl, etc., but the examples of the alkynyl are not limited thereto.

Term: ⌈Cycloalkenyl⌋ described in the present invention means a non-aromatic monocyclic or polycyclic hydrocarbon ring radical containing at least one carbon-carbon double bond, and examples of the cycloalkenyl group include cyclopentenyl, cyclobutenyl, cyclohexenyl, etc., but the examples of the cycloalkenyl are not limited thereto.

In the polymer for preparing the resist underlayer film according to an exemplary embodiment of the present invention, $R_5$ may be (C4-30)bicycloalkyl, (C5-30)tricycloalkyl or (C6-C30)tetracycloalkyl, and preferably, norbornyl, bicyclohexyl, tricyclohexyl, adamantyl or decalinyl.

The polymer for preparing the resist underlayer film according to an exemplary embodiment of the present invention may be exemplified as polymers including repeating units each selected from Chemical Formulas 1-1 to 1-26 below:
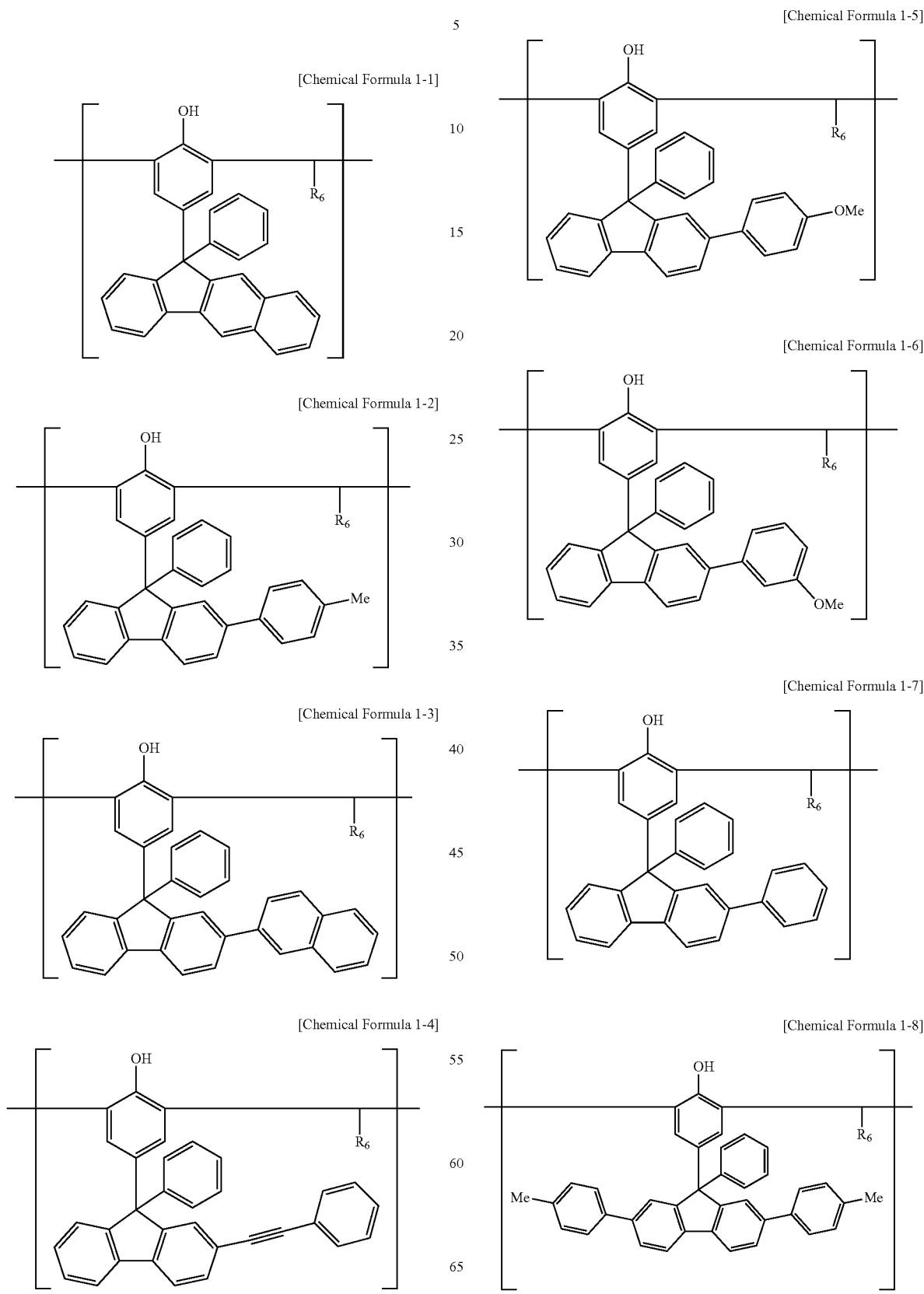

[Chemical Formula 1-9]
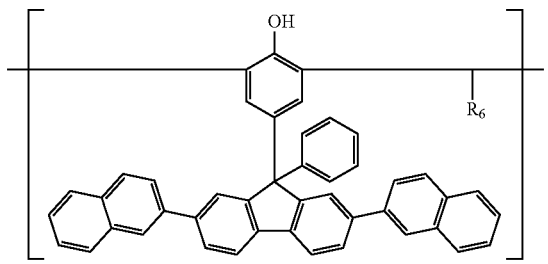
[Chemical Formula 1-10]
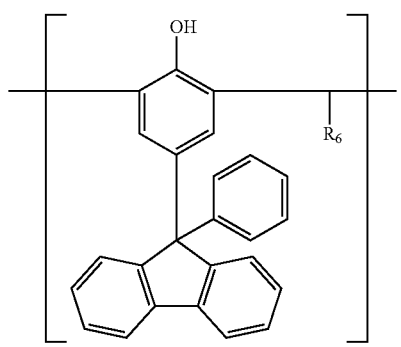
[Chemical Formula 1-11]
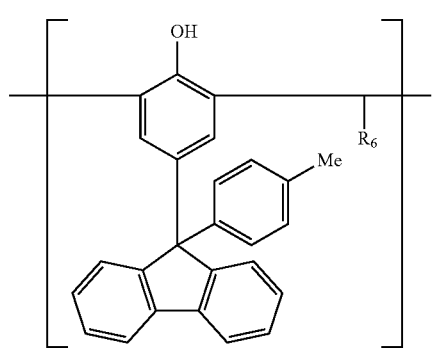
[Chemical Formula 1-12]
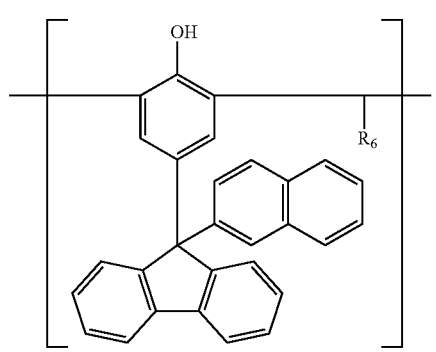
[Chemical Formula 1-13]
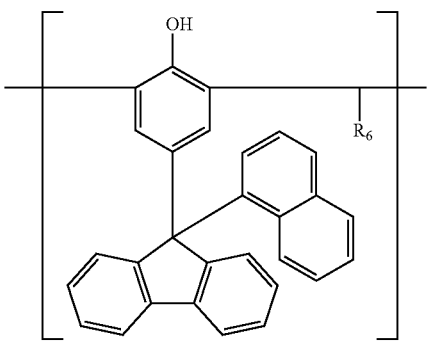
[Chemical Formula 1-14]
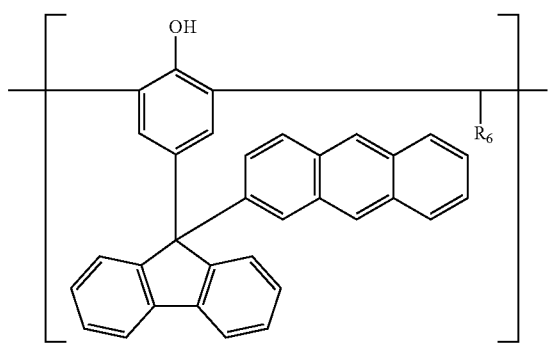
[Chemical Formula 1-15]
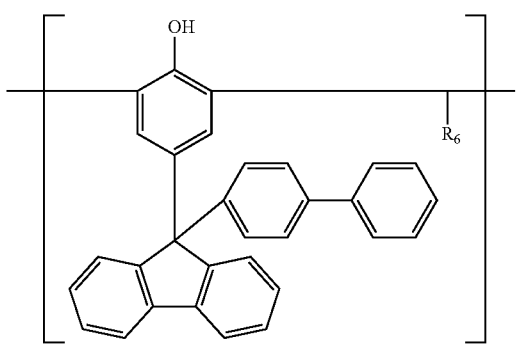
[Chemical Formula 1-16]
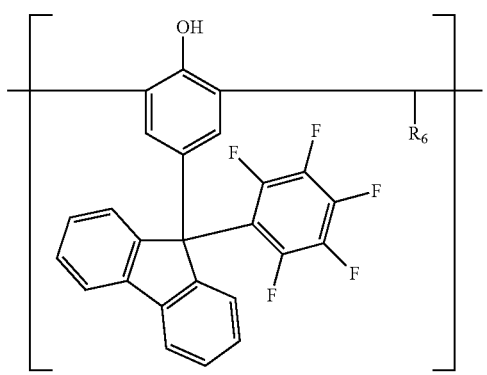

[Chemical Formula 1-17]
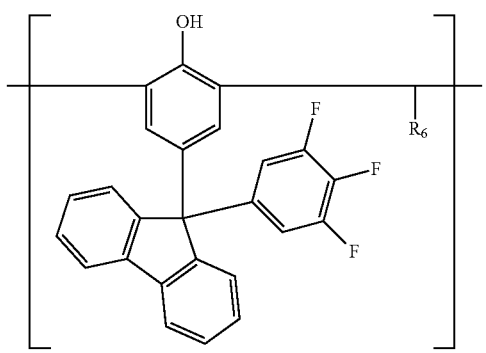
[Chemical Formula 1-18]
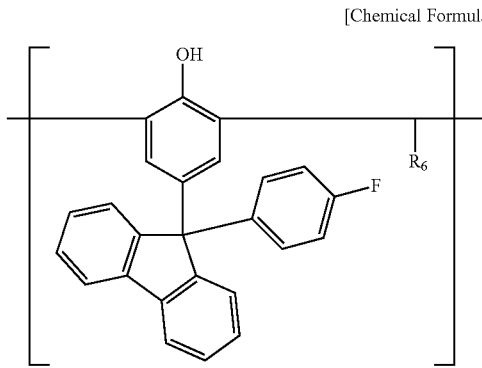
[Chemical Formula 1-19]
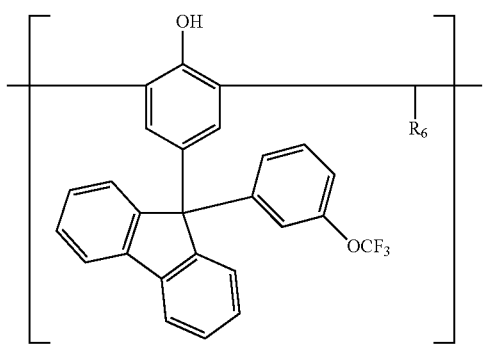
[Chemical Formula 1-20]
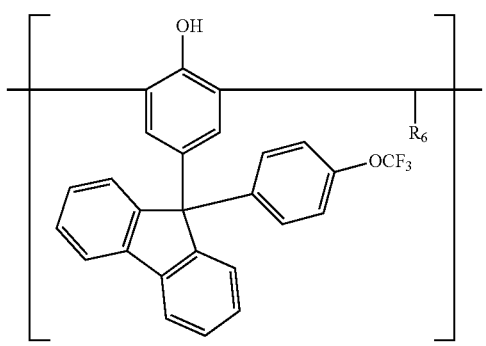
[Chemical Formula 1-21]
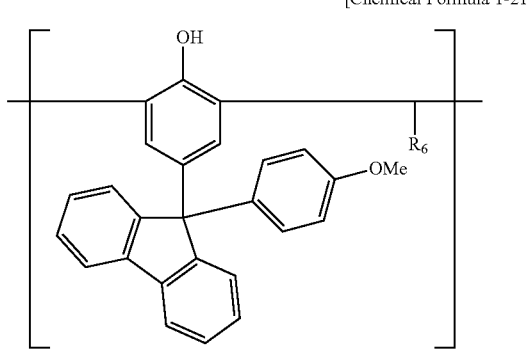
[Chemical Formula 1-22]
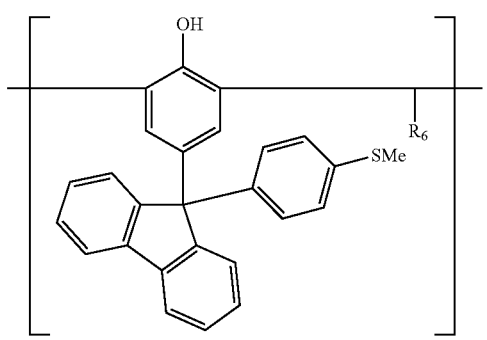
[Chemical Formula 1-23]
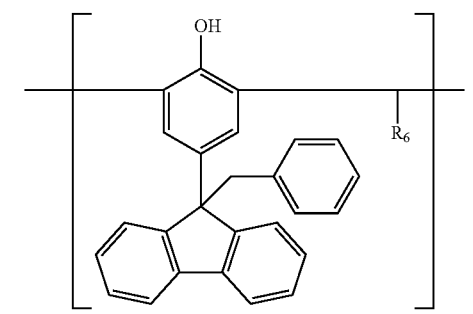
[Chemical Formula 1-24]
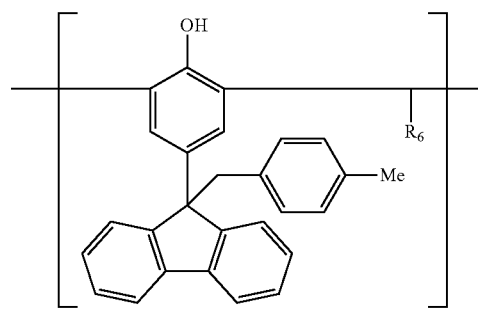

[Chemical Formula 1-25]

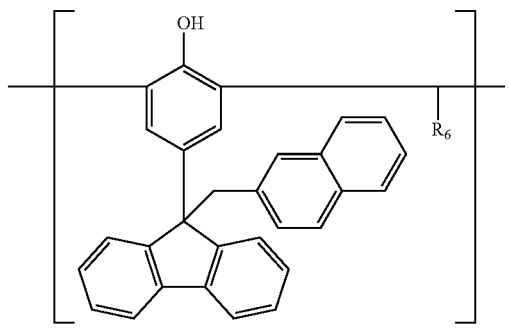

[Chemical Formula 1-26]

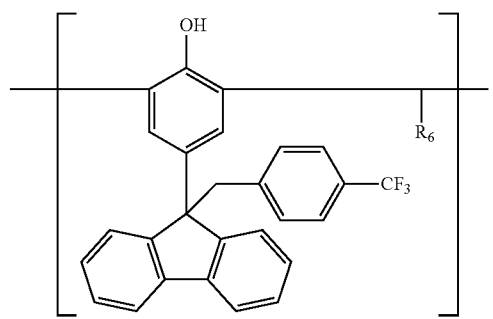

$R_6$ is hydrogen, (C1-C10)alkyl, (C3-C10)cycloalkyl or (C6-C20)aryl, and the alkyl, cycloalkyl, or aryl of $R_6$ may be further substituted with one or more substituents selected from the group consisting of (C1-C10)alkyl and (C6-C20)aryl.

The polymer for preparing the resist underlayer film according to an exemplary embodiment of the present invention may further include another repeating unit, specifically, a repeating unit represented by Chemical Formula 3 below:

[Chemical Formula 3]

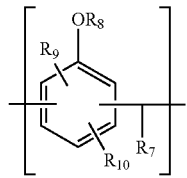

in Chemical Formula 3, $R_7$ is hydrogen, (C1-C10)alkyl, (C3-C10)cycloalkyl or (C6-C20)aryl, and the alkyl, cycloalkyl, or aryl of $R_7$ may be further substituted with one or more substituents selected from the group consisting of (C1-C10)alkyl and (C6-C20)aryl;

$R_8$ is hydrogen, (C1-C10)alkyl, (C3-C10)cycloalkyl, (C6-C20)aryl, (C1-C10)alkyl(C6-C20)aryl or (C6-C20)aryl(C1-C10)alkyl;

$R_9$ and $R_{10}$ are each independently hydrogen, (C1-C10)alkyl, (C3-C10)cycloalkyl, (C6-C20)aryl, (C1-C10)alkoxy, (C6-C20)aryloxy, (C1-C10)alkyl(C6-C20)aryl or (C6-C20)aryl(C1-C10)alkyl.

The polymer for preparing the resist underlayer film according to an exemplary embodiment of the present invention may simultaneously include the repeating unit represented by Chemical Formula 1 and the repeating unit represented by Chemical Formula 3, thereby easily performing a hard mask process having excellent etching resistance, thermal stability, coating uniformity, surface planarization, uniformity of pattern edges, and mechanical properties of patterns, or a planarization process of a wafer surface.

The polymer for preparing the resist underlayer film according to an exemplary embodiment of the present invention may be obtained in a novolak resin type by condensation reaction of the fluoreneol-based monomer represented by Chemical Formula 2 below and an aldehyde monomer represented by Chemical Formula A below in the presence of an acid catalyst:

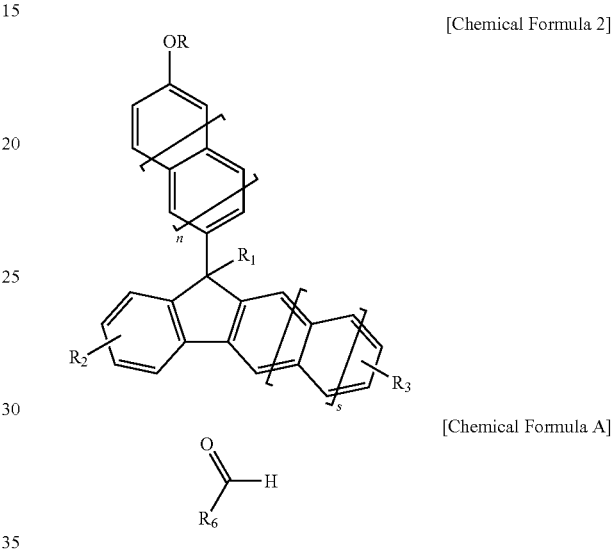

[Chemical Formula 2]

[Chemical Formula A]

in Chemical Formulas 2 and A, R, $R_1$ to $R_3$, n, s and $R_6$ are the same as previously defined in Chemical Formula 1 above.

In the polymer for preparing the resist underlayer film according to an exemplary embodiment of the present invention, the aldehyde monomer represented by Chemical Formula A may be various aldehyde monomers such as formaldehyde, acetaldehyde, propionaldehyde, butyraldehyde, isobutyraldehyde, valeraldehyde, isovaleraldehyde, pivaline aldehyde, caprone aldehyde, 2-methylbutyl aldehyde, undecyl aldehyde, cyclopropane aldehyde, cyclobutane aldehyde, cyclopentane aldehyde, cyclohexane aldehyde, cycloheptane aldehyde, benzaldehyde, naphthyl aldehyde, anthryl aldehyde, phenanthryl aldehyde, phenyl acetaldehyde, 3-phenyl propionaldehyde, methyl benzaldehyde, ethyl benzaldehyde, butyl benzaldehyde, etc., and preferably, formaldehyde, acetaldehyde, benzaldehyde or naphthyl aldehyde.

In the polymer for preparing the resist underlayer film according to an exemplary embodiment of the present invention, an amount of the aldehyde monomer represented by Chemical Formula A may be 0.5 to 5 mol, preferably, 0.55 to 3 mol, and more preferably, 0.6 to 2 mol, based on 1 mol of the fluoreneol-based monomer represented by Chemical Formula 2. When the amount of the aldehyde monomer represented by Chemical Formula A is more than 5 mol, a molecular weight is rapidly increased, such that it is difficult to control the molecular weight, and when the amount of the aldehyde monomer represented by Chemical Formula A is less than 0.5 mol, the molecular weight is excessively low, such that the polymer may not be obtained.

In the polymer for preparing the resist underlayer film according to an exemplary embodiment of the present invention, the acid catalyst used in the condensation reaction may be conventional acid catalysts, for example, acidic catalysts such as hydrochloric acid, nitric acid, sulfuric acid, formic acid, oxalic acid, acetic acid, phosphoric acid, perchloric acid, methanesulfonic acid, p-toluenesulfonic acid, trifluoromethanesulfonic acid, etc. The acid having strong acidity is difficult to control a molecular weight, and the acid having weak acidity has a significantly low molecular weight, such that it is difficult to obtain the polymer and a reaction time is long. At the time of preparing the polymer, the amount of the acid catalyst is 0.002 to 0.02 mol, and preferably, 0.005 to 0.010 mol, based on 1 mol of the fluoreneol-based monomer represented by Chemical Formula 2. When the amount of the acid catalyst is more than 0.02 mol, it may be difficult to control the molecular weight. When the amount of the acid catalyst is less than 0.002 mol, a reaction progress speed may be slow, and a reaction time may be largely consumed, and the polymer may not be obtained.

In the polymer for preparing the resist underlayer film according to an exemplary embodiment of the present invention, the condensation reaction is performed even without a solvent, but is performed by using conventional solvents. The above solvents may be used without specific limitation as long as they are conventional organic solvents that are capable of dissolving the monomer, etc., while not disturbing the reaction. For example, organic solvents such as tetrahydrofuran, dioxane, toluene, xylene, 1,2,3,4-tetrahydronaphthalene (THN), etc., may be used. A temperature for the condensation reaction is generally 40° C. to 200° C., and a time for the condensation reaction may be variously selected according to reaction temperature. As the condensation reaction methods, there are a method for integrally introducing the fluoreneol-based monomer represented by Chemical Formula 2, the aldehyde monomer represented by Chemical Formula A, and an acid catalyst, or a method for dropwise-adding the fluoreneol-based monomer represented by Chemical Formula 2 and the aldehyde monomer represented by Chemical Formula A in the presence of the acid catalyst.

In the polymer for preparing the resist underlayer film according to an exemplary embodiment of the present invention, the repeating unit represented by Chemical Formula 3 is obtained in a novolak resin type by condensation reaction of various phenol monomers and an aldehyde monomer in the presence of an acid catalyst as the same as the preparation of the repeating unit represented by Chemical Formula 1.

A polystyrene-conversion weight average molecular weight (Mw) by gel permeation chromatography (GPC) of the polymer for preparing the resist underlayer film according to an exemplary embodiment of the present invention may be 500 or more, but may be 500 to 20,000, and more preferably, 1,000 to 10,000 in view of preparation of the underlayer film composition, easiness of handling, film formation, and uniformity. When the weight average molecular weight of the polymer is less than 500, coating uniformity may be decreased.

In addition, the present invention provides a resist underlayer film composition containing the polymer for preparing the resist underlayer film including the repeating unit represented by Chemical Formula 1.

The resist underlayer film composition according to an exemplary embodiment of the present invention may be used as a hard mask in a multilayer semiconductor lithography process.

The resist underlayer film composition according to an exemplary embodiment of the present invention may form an underlayer film on the substrate such as a silicon wafer, etc., by spin-coating, spin on carbon (SOC) methods, etc., and may further include the polymer for preparing the resist underlayer film and an organic solvent.

In the resist underlayer film composition according to an exemplary embodiment of the present invention, the polymer for preparing the resist underlayer film may have an amount of 0.5 to 50 wt %, preferably, 1 to 30 wt %, and more preferably, 2 to 20 wt %, based on total amount of the resist underlayer film composition. When the polymer for preparing the resist underlayer film is used within the above-described range, solubility of the resist underlayer film composition and coating property at the time of forming a film may be excellent. When the amount of the polymer for preparing the resist underlayer film is less than 0.5 wt %, an underlayer film having a desired thickness may not be formed, and when the amount of the polymer for preparing the resist underlayer film is more than 50 wt %, the underlayer film may not be uniformly formed.

The resist underlayer film composition according to an exemplary embodiment of the present invention may further include at least one additive selected from crosslinking agents, acid catalysts, acid generators, antifoaming agents, and surfactants.

The polymer for preparing the resist underlayer film including the repeating unit represented by Chemical Formula 1 according to an exemplary embodiment of the present invention may be dissolved in the organic solvent to be coated on the wafer, and then, a crosslinking reaction may be performed at a high temperature by itself. However, the crosslinking reaction is generally performed by adding a crosslinking agent and an acid catalyst. The composition obtained after the polymer for preparing the resist underlayer film, the crosslinking agent, and the acid catalyst are dissolved in a solvent, is subjected to a filtration process so that particulate impurities are completely removed.

In the resist underlayer film composition according to an exemplary embodiment of the present invention, the organic solvent to be usable may be any organic solvent as long as the polymer for preparing the resist underlayer film including the repeating unit represented by Chemical Formula 1, the crosslinking agent, and the acid catalyst are easily dissolved therein. The organic solvent is an organic solvent generally used for a process for manufacturing a semiconductor, and may include cyclohexanone, 2-heptanone, propyleneglycol monomethyl ether, propyleneglycol monomethyl acetate, propyleneglycol monomethyl ether acetate, gamma-butyrolactone, ethyl lactate, dimethylsulfoxide, dimethylacetamide, N-methylpyrrolidone, and mixtures thereof, etc.

In the resist underlayer film composition according to an exemplary embodiment of the present invention, the crosslinking agent is to induce the crosslinking reaction to better cure the underlayer film. The crosslinking agent usable in the resist underlayer film composition of the present invention may be conventional crosslinking agents of melamine type, epoxy type, etc., and for example, at least one selected from compounds represented by Chemical Formulas 4-1 to 4-7 below:

[Chemical Formula 4-1]

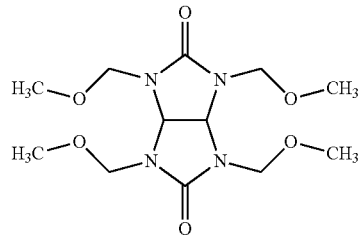

[Chemical Formula 4-2]

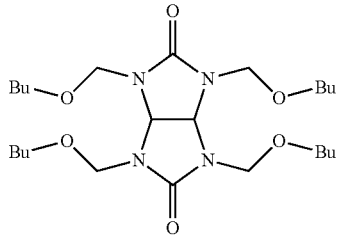

[Chemical Formula 4-3]

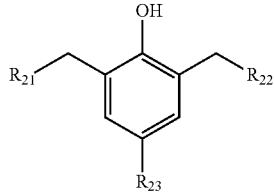

in Chemical Formula 4-3, $R_{21}$ and $R_{22}$ are each independently hydroxy or (C1-C3)alkoxy, and $R_{23}$ is (C1-C10)alkyl,

[Chemical Formula 4-4]

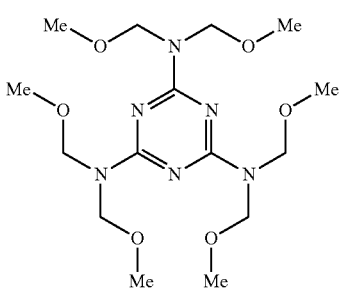

[Chemical Formula 4-5]

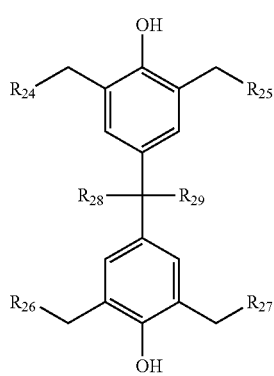

in Chemical Formula 4-5, $R_{24}$, $R_{25}$, $R_{26}$ and $R_{27}$ are each independently hydroxy or (C1-C3)alkoxy, and $R_{28}$ and $R_{29}$ are each independently hydrogen, (C1-C10)alkyl or halo (C1-C10)alkyl,

[Chemical Formula 4-6]

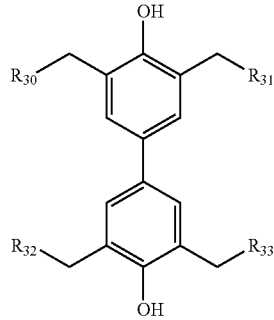

in Chemical Formula 4-6, $R_{30}$, $R_{31}$, $R_{32}$ and $R_{33}$ are each independently hydroxy or (C1-C3)alkoxy, and

[Chemical Formula 4-7]

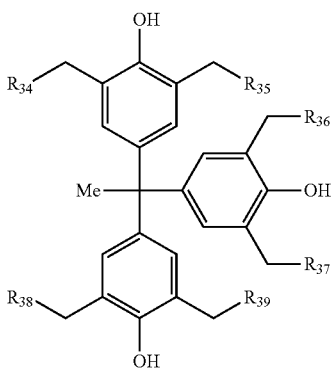

in Chemical Formula 4-7, $R_{34}$, $R_{35}$, $R_{36}$, $R_{37}$, $R_{38}$ and $R_{39}$ are each independently hydroxy or (C1-C3)alkoxy.

In the resist underlayer film composition according to an exemplary embodiment of the present invention, a cross-linking agent to be usable may be specifically exemplified by the following structures:

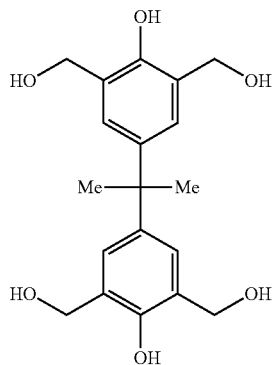

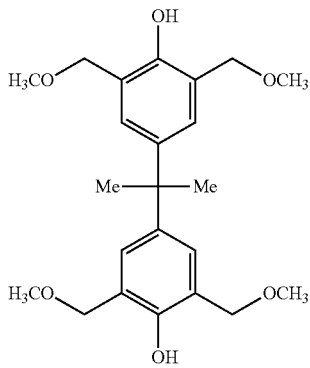
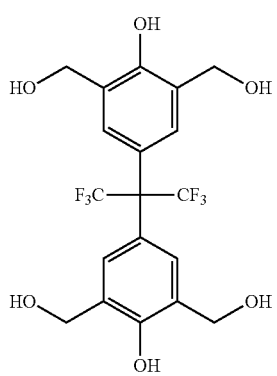
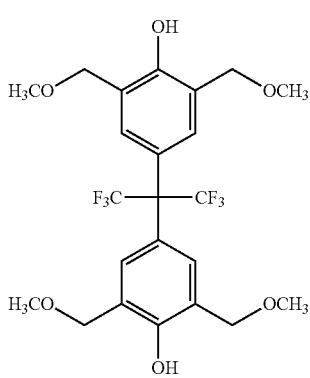
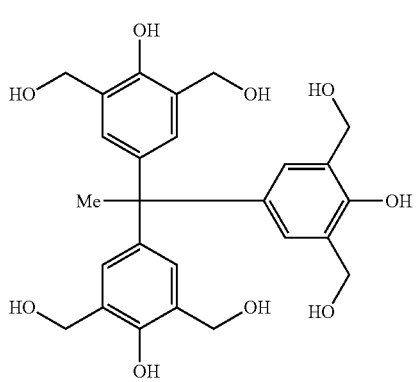

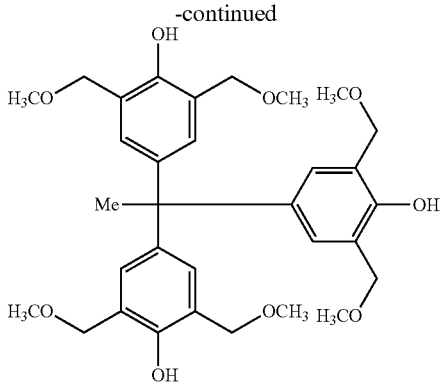
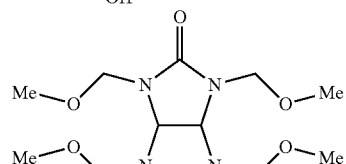
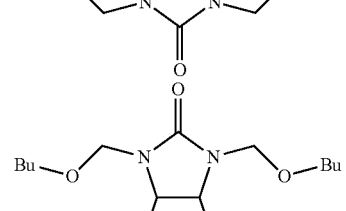
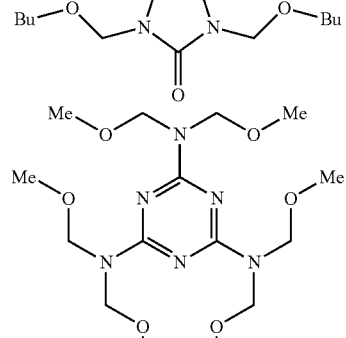
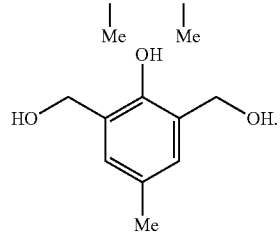

In the resist underlayer film composition according to an exemplary embodiment of the present invention, an amount of the crosslinking agent may be slightly different depending on the kinds of crosslinking agents, but the amount of the crosslinking agent may be 0.1 to 30 parts by weight, preferably, 0.1 to 20 parts by weight, and more preferably, 0.5 to 10 parts by weight, based on 100 parts by weight of the polymer for preparing the resist underlayer film including the repeating unit represented by Chemical Formula 1 of the present invention. When the amount of the crosslinking agent is excessively small, crosslinking is not sufficiently performed, such that the crosslinking agent is dissolved in a solvent during a process of coating organic materials at an upper part, and when the amount of the crosslinking agent is excessively large, the crosslinking agent remains after the crosslinking, such that fume largely occurs, whereby stability of the resist may be decreased.

In the resist underlayer film composition according to an exemplary embodiment of the present invention, a cross-linking catalyst may be used to increase a crosslinking speed in the crosslinking process. As the crosslinking catalyst, the acid catalyst or the acid generator more advantageously functions as compared to a basic catalyst. The acid generator generates acid by pyrolysis, but may generate acid by light irradiation.

In the composition for preparing the resist underlayer film composition according to an exemplary embodiment of the present invention, the acid catalyst or the acid generator is added to reduce a temperature of the crosslinking reaction of the polymer and improve a crosslinking rate. The acid catalyst or the acid generator usable in the present invention is not limited, but for example, may be at least one selected from compounds represented by Chemical Formulas 5-1 to 5-6 below:

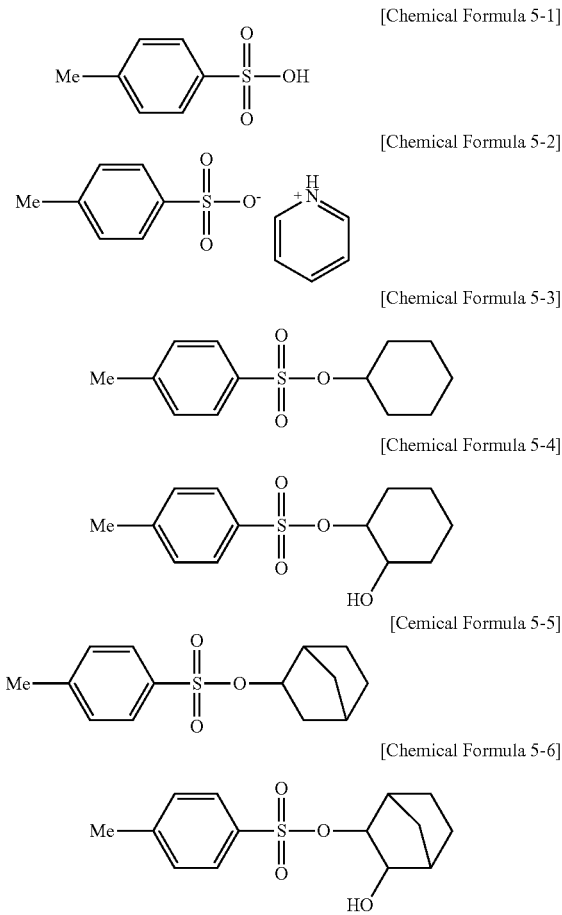

[Chemical Formula 5-1]

[Chemical Formula 5-2]

[Chemical Formula 5-3]

[Chemical Formula 5-4]

[Cemical Formula 5-5]

[Chemical Formula 5-6]

In the resist underlayer film composition according to an exemplary embodiment of the present invention, the acid catalyst may be divided into strong acids such as toluenesulfonic acid, and potential acid generators that are decomposed by heat to generate acid. In preparing the composition, it is preferred to use the potential acid generators rather than using the strong acids such as toluenesulfonic acid in view of storage stability. When the strong acids are used, storage stability of the resist underlayer film composition is decreased. An amount of the acid catalyst or the acid generator may be 0.01 to 10 parts by weight, preferably, 0.05 to 5 parts by weight, and more preferably, 0.1 to 5 parts by weight, based on 100 parts by weight of the polymer for preparing the resist underlayer film including the repeating unit represented by Chemical Formula 1. When the amount thereof is excessively small, a curing speed is slow. Meanwhile, when the amount thereof is excessively large, physical properties of a cured product may be decreased. In particular, when strength of the acid is large or great, fume largely occurs.

In the resist underlayer film composition according to an exemplary embodiment of the present invention, the surfactant may be used to improve coating uniformity at the time of forming the resist underlayer film. As the surfactant, commercially available surfactants such as sulfinol-series (Air Products and Chemicals, Inc.), F-series (F-410, F-444, F-477, R-08, R-30, etc., from DIC), etc., may be used. When the surfactant is used, the surfactant may have a content of 0.1 to 1 part by weight, preferably 0.2 to 0.8 parts by weight, based on 100 parts by weight of the total resist underlayer film composition. When the content of the surfactant is more than 1 part by weight, based on 100 parts by weight of the total resist underlayer film composition, resist film quality may be poor. The resist underlayer film composition according to the present invention may be prepared by blending the components according to general methods.

The resist underlayer film composition according to an exemplary embodiment of the present invention may have a film-forming property in which the film is capable of being formed by general spin-coating.

In addition, the present invention provides a method for forming a resist underlayer film using the resist underlayer film composition.

The method for forming the resist underlayer film according to an exemplary embodiment of the present invention may include: forming a coating layer by spin-coating the resist underlayer film composition on a wafer; and forming a resist underlayer film by heating the wafer on which the coating layer is formed.

In the method for forming the resist underlayer film according to an exemplary embodiment of the present invention, a coating thickness of the resist underlayer film composition is not specifically limited, but the resist underlayer film composition may be spin-coated at a thickness of 50 to 20,000 Å on an upper part of a substrate. In addition, the resist underlayer film may be formed by heating the wafer at a heating temperature of 200 to 450° C., preferably, 300 to 400° C. for 30 seconds to 5 minutes. The resist underlayer film formed as formed above has a thickness of about 30 to 18,000 Å. After the heating process is finished, the wafer is used for a next process. In addition, the coating process, the thickness of the underlayer film, the heating temperature and time are not limited to the above-described ranges, but may vary to prepare various resist underlayer films that are different from each other depending on purposes.

In the method for forming the resist underlayer film according to an exemplary embodiment of the present invention, the resist underlayer film composition of the present invention includes the polymer for preparing the resist underlayer film including the repeating unit represented by Chemical Formula 1, thereby having excellent etching resistance, thermal stability, coating uniformity, surface planarization, uniformity of pattern edges, and mechanical properties of patterns, such that the resist underlayer film composition of the present invention is applicable to a hard mask process or a planarization process of a wafer surface. Further, the resist underlayer film composition of the present invention has high solubility to organic solvents even though the polymer for preparing the resist underlayer film including the repeating unit represented by Chemical Formula 1 has a high carbon content, thereby achieving remarkably improved storage stability and line compatibility in a semiconductor process.

Further, the present invention provides a method for forming patterns using the resist underlayer film composition.

The method for forming patterns according to an exemplary embodiment of the present invention may include: 1) forming a resist underlayer film by using the resist underlayer film composition of the present invention on an upper part of a substrate; 2) forming a photoresist layer on the upper part of the resist underlayer film; 3) exposing the photoresist layer to radiation with predetermined patterns to produce patterns of a region exposed to the radiation on the photoresist layer; 4) selectively removing the photoresist layer and the resist underlayer film according to the patterns to expose the substrate in a shape of the patterns; and 5) etching an exposed part of the substrate.

In the method for forming patterns according to an exemplary embodiment of the present invention, the substrate may be conventionally usable substrates, for example, a silicon wafer, a glass substrate or a polymer substrate.

In the method for forming patterns according to an exemplary embodiment of the present invention, before step 2) above, a conventional silicon-containing resist underlayer film (inorganic underlayer film) or a bottom anti-refractive coating (BARC) film may be further formed on the upper part of the resist underlayer film. The silicon-containing resist underlayer film (inorganic underlayer film) may be made of silicon nitride, silicon oxide or silicon oxynitride (SiON). In addition, the method for forming patterns according to an exemplary embodiment of the present invention may further include forming a bottom anti-refractive coating (BARC) film on the silicon-containing resist underlayer film.

In the method for forming patterns according to an exemplary embodiment of the present invention, the producing of the patterns on the photoresist layer may be performed by development using conventional alkaline aqueous solutions such as a tetramethylammonium hydroxide (TMAH) developer, etc., and the removing of the resist underlayer film may be performed by dry etching using $CHF_3/CF_4$ mixed gas, etc., and the etching of the substrate may be performed by plasma etching using $Cl_2$ or HBr gas. Here, the etching method, etc., are not limited to the above-described methods, but may be variously changed according to process conditions.

The resist underlayer film formed by the present invention is formed by the polymer for preparing the resist underlayer film including the repeating unit represented by Chemical Formula 1 having excellent thermal stability, etching resistance, and coating uniformity, and has excellent thermal stability and etching resistance, and excellent gap-fill performance, and excellent planarization even when being applied on the wafer having steps.

Further, the present invention provides a fluoreneol-based monomer represented by Chemical Formula 2 below, as a monomer for preparing the polymer for preparing the resist underlayer film including the repeating unit represented by Chemical Formula 1:

[Chemical Formula 2]

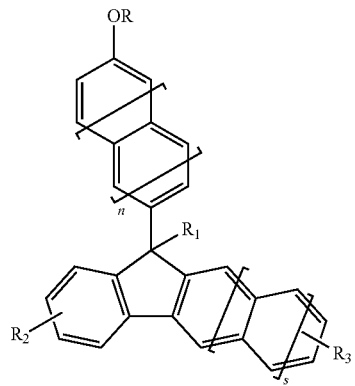

in Chemical Formula 2,

R is hydrogen, (C1-C10)alkyl, (C3-C10)cycloalkyl, (C6-C20)aryl, (C1-C10)alkyl(C6-C20)aryl or (C6-C20)aryl(C1-C10)alkyl;

$R_1$ is

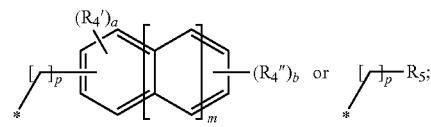

$R_4'$ and $R_4''$ are each independently hydrogen, (C1-C10)alkyl, (C3-C10)cycloalkyl, (C2-C10)alkenyl, (C3-C10)cycloalkenyl, (C2-C10)alkynyl, 4- to 10-membered heterocycloalkyl, (C6-C20)aryl, (C3-C20)heteroaryl, halogen, cyano, (C1-C10)alkoxy, (C3-C10)cycloalkoxy, (C6-C20)aryloxy, (C1-C10)alkylthio, (C3-C10)cycloalkylthio, (C6-C20)arylthio, (C1-C10)alkylcarbonyl, (C2-C10)alkenylcarbonyl, (C6-C20)arylcarbonyl, (C3-C10)cycloalkylcarbonyl, or (C3-C10)cycloalkenylcarbonyl;

$R_5$ is non-aromatic polycyclic (C3-C30)cycloalkyl;

$R_2$ and $R_3$ are each independently hydrogen, (C1-C10)alkyl, (C3-C10)cycloalkyl, (C2-C10)alkenyl, (C3-C10)cycloalkenyl, (C2-C10)alkynyl, 4- to 10-membered heterocycloalkyl, (C6-C20)aryl, (C3-C20)heteroaryl, halogen, cyano, (C1-C10)alkoxy, (C3-C10)cycloalkoxy, (C6-C20)aryloxy, (C1-C10)alkylthio, (C3-C10)cycloalkylthio, (C6-C20)arylthio, (C1-C10)alkylcarbonyl, (C2-C10)alkenylcarbonyl, (C6-C20)arylcarbonyl, (C3-C10)cycloalkylcarbonyl, or (C3-C10)cycloalkenylcarbonyl;

the alkyl, cycloalkyl, alkenyl, cycloalkenyl, alkynyl, heterocycloalkyl, aryl, heteroaryl, alkoxy, cycloalkoxy, aryloxy, alkylthio, cycloalkylthio, arylthio, alkylcarbonyl, alkenylcarbonyl, arylcarbonyl, cycloalkylcarbonyl, or cycloalkenylcarbonyl of $R_4'$, $R_4''$, $R_2$ and $R_3$ may be further substituted with one or more substituents selected from the group consisting of halogen, cyano, nitro, (C1-C10)alkyl, (C3-C10)cycloalkyl, (C6-C20)aryl, (C3-C20)heteroaryl, (C1-C10)alkoxy, (C6-C20)aryloxy, halo(C1-C10)alkyl and halo(C1-C10)alkoxy;

a is an integer of 1 to 3, and when a is an integer of 2 or more, each $R_4'$ may be the same as each other or different from each other;

b is an integer of 1 or 2, and when b is an integer of 2, each $R_4''$ may be the same as each other or different from each other;

p is an integer of 0 to 7;

m is an integer of 0 to 4;
n is an integer of 0 to 4;
s is an integer of 0 to 4; and
the heteroaryl and the heterocycloalkyl include one or more heteroatoms selected from B, N, O, S, P(=O), Si, Se and P.

The fluoreneol-based monomer according to an exemplary embodiment of the present invention may be prepared by reacting a ketone derivative (a) and Grignard reagent (b) to prepare a hydroxy derivative (c), followed by reaction with a phenol derivative (d) as shown in the following Reaction Scheme 1, but the present invention is not limited thereto. In addition to the above-described method, any known methods may be applied as long as the final structure is the same.

may be added to the prepared alcohol (c) under condition of ethers such as diethyl ether, tetrahydrofuran, and dioxane, halogen-substituted solvents such as chloroform, methylene chloride, and carbon tetrachloride, and organic acid solvents such as acetic acid, and then the phenol derivative (d) may be added in an amount of 1.0 to 10.0 equivalent, thereby preparing a desirable fluoreneol-based monomer represented by Chemical Formula 2.

The fluoreneol-based monomer according to an exemplary embodiment of the present invention may be exemplified by the following structures, but the present invention is not limited thereto:

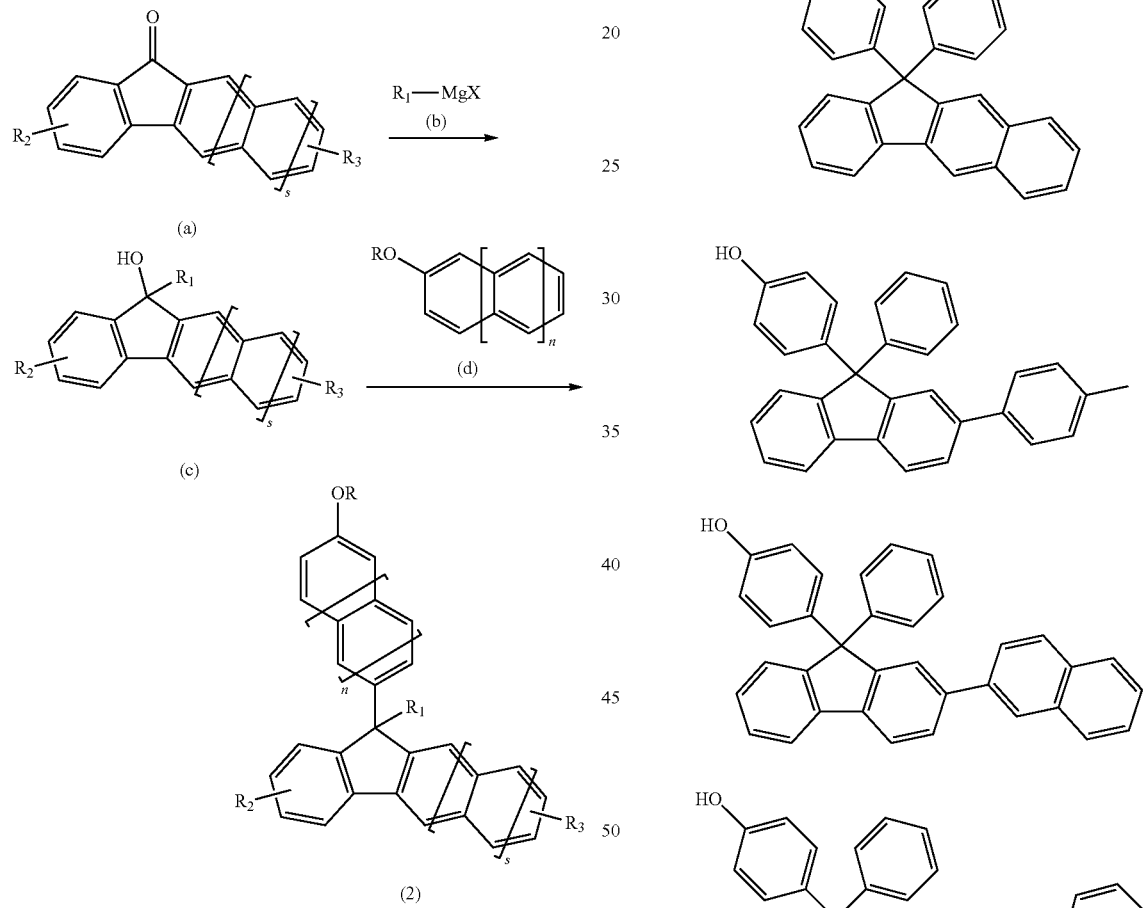

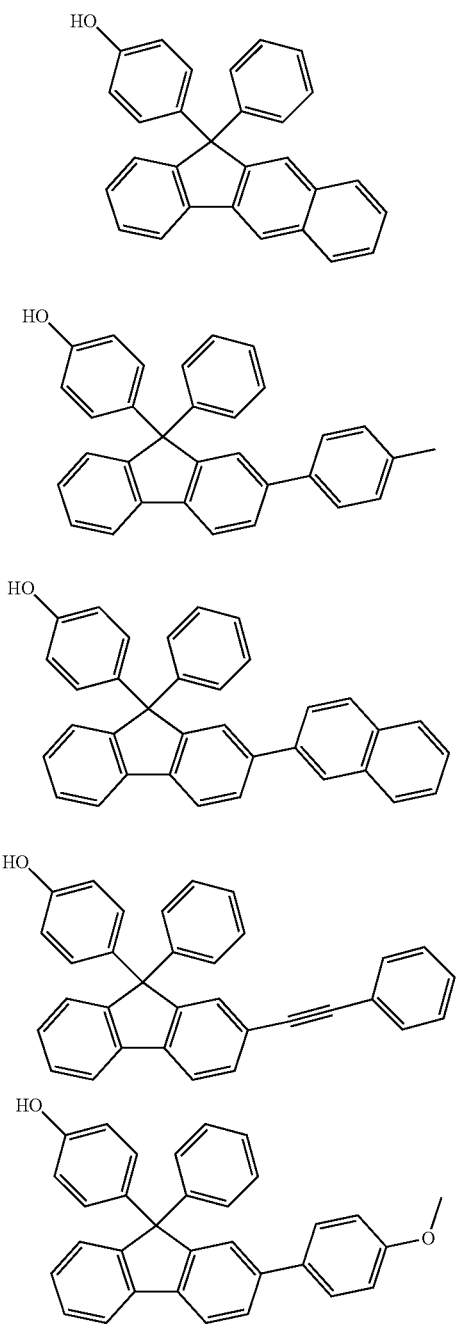

in Reaction Scheme 1, R, $R_1$ to $R_3$, n and s are the same as previously defined in Chemical Formula 2 above.

In Reaction Scheme 1, the Grignard reagent (b) may be used in an amount of 1.0 to 5.0 equivalents relative to the reactant ketone (a), wherein ethers such as diethyl ether, tetrahydrofuran, and dioxane, hydrocarbons such as hexane and heptane, aromatic hydrocarbons such as benzene and toluene, etc., may be used as solvents. Desirable alcohol (c) may be prepared at a reaction temperature of −78-80° C. Organic/inorganic acid such as sulfuric acid, trifluoroacetic acid, hydrochloric acid, hydrogen bromide, hydrogen iodide, nitric acid, phosphoric acid, chromic acid, methanesulfonic acid, etc., in an amount of 0.01 to 1.0 equivalent -continued
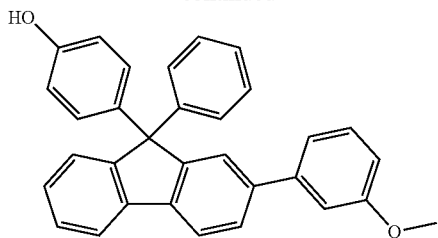
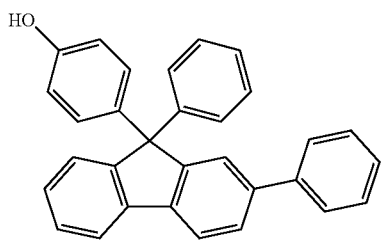
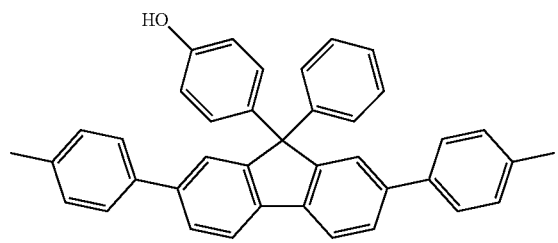
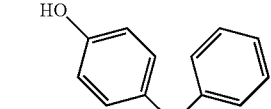
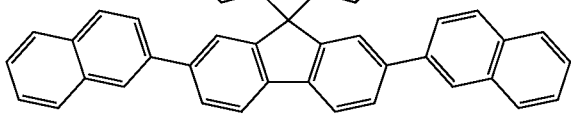
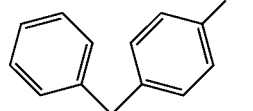
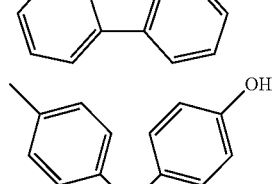
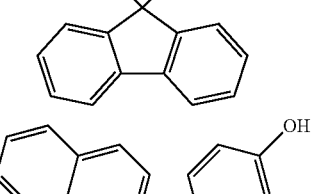
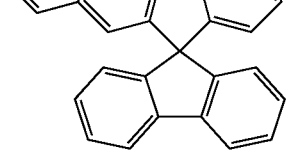
-continued
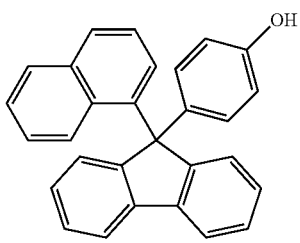
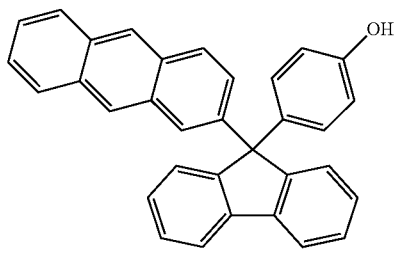
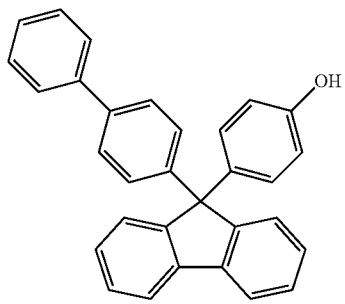
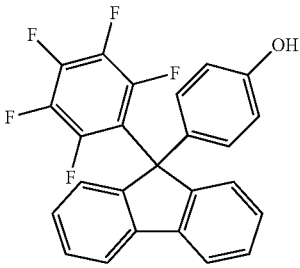
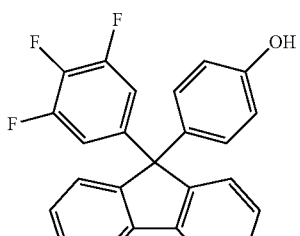
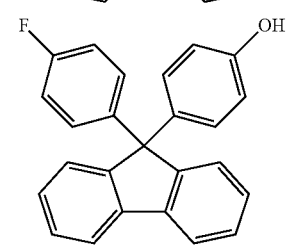

-continued

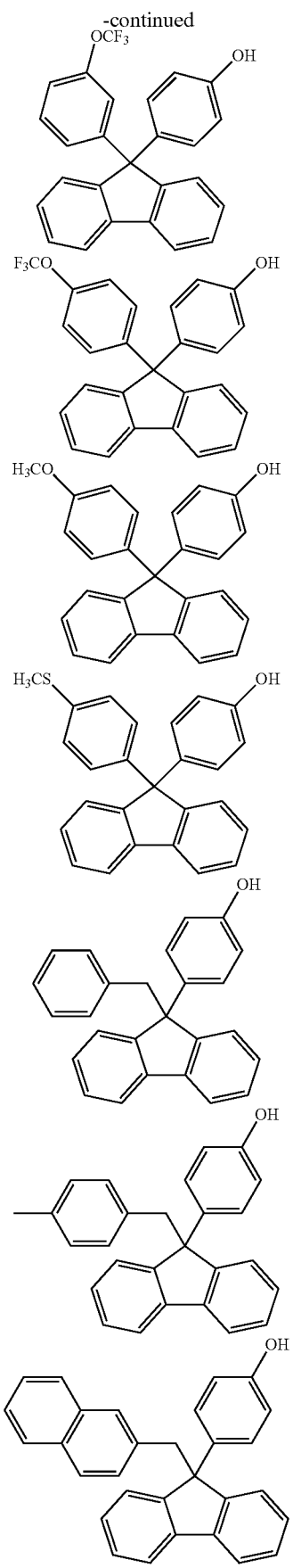

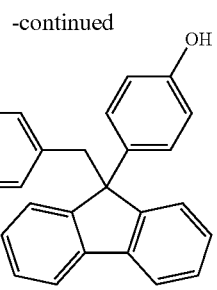

Hereinafter, the present invention is described through specific Examples, and Comparative Examples in detail. The following Examples are provided for merely exemplifying the present invention, and therefore, the scope of the present invention is not limited to the following Examples.

[Synthesis Example 1] Synthesis of 4-[9-(4-methoxyphenyl)-9H-fluorene-9-yl]phenol 9,9-bis(4-hydroxyphenyl) fluorene (20 g) and potassium carbonate (8.68 g) were added to a dimethylformamide solvent (120 mL). Iodomethane (3.6 ml) was added thereto at room temperature, and stirred for 18 hours. After the reaction, the resultant mixture was diluted with diethylether, and an organic layer was washed with water once and then washed with saturated sodium chloride aqueous solution twice. The extracted organic solvent layer was removed by distillation under reduced pressure, and purified by silica gel column chromatography to obtain high purity of 4-[9-(4-methoxyphenyl)-9H-fluorene-9-yl]phenol (9.6 g).
$^1$H NMR (CDCl$_3$, 500 MHz) δ 7.75 (d, 2H), 7.38-7.33 (m, 4H), 7.28-7.25 (m, 2H), 7.12 (d, 2H), 7.07 (d, 2H), 6.75 (d, 2H), 6.67 (d, 2H), 4.76 (s, 1H), 3.75 (s, 3H)

[Synthesis Example 2] Synthesis of 4-(9-phenyl-9H-fluorene-9-yl)phenol

Phenol (7.2 g) and sulfuric acid (0.5 ml) were added to a dichloromethane solvent (50 ml). 9-phenyl-9H-fluorene-9-ol (10 g) was added thereto at room temperature, followed by stirring for 1 hour to perform the reaction. After the reaction, an organic layer was washed with water once and 1N sodium hydroxide aqueous solution twice. An organic solvent was removed by distillation under reduced pressure, and high purity of 4-(9-phenyl-9H-fluorene-9-yl)phenol (8 g) was secured through toluene recrystallization.
$^1$H NMR (CDCl$_3$, 500 MHz) δ 7.77 (d, 2H), 7.40 (d, 2H), 7.38-7.35 (m, 2H), 7.28 (d, 2H), 7.27 (m, 5H), 7.09 (d, 2H), 6.69 (d, 2H), 4.62 (s, 1H)

[Synthesis Example 3] Synthesis of 4-[9-(naphthalene-2-yl)-9H-fluorene-9-yl]phenol 9-fluorenone (9.0 g) was added to a tetrahydrofuran solvent (90 ml). 0.5 M 2-naphthyl magnesium bromide tetrahydrofuran solution (106 ml) was slowly added at 0° C. After the addition was completed, the reaction mixture was stirred at room temperature for 6 hours. After the reaction was completed, a saturated ammonium chloride aqueous solution was added to complete the reaction. An organic layer was separated and was washed with water once, and residual water was removed with anhydrous magnesium sulfate. An organic solvent was removed by distillation under reduced pressure, and high purity of 9-(naphthalene-2-yl)-9H-fluorene-9-ol was secured through toluene/heptane recrystallization. Phenol (7.2 g) and sulfuric acid (0.5 ml) were added to a dichloromethane solvent (50 ml). 9-(naphthalene-2-yl)-9H-fluorene-9-ol (10 g) was added thereto at room temperature, followed by stirring for 1 hour to perform the reaction. After the reaction, an organic layer was washed with water once and 1N sodium hydroxide aqueous solution twice. An organic solvent was removed by distillation under reduced pressure, and high purity of 4-[9-(naphthalene-2-yl)-9H-fluorene-9-yl)phenol (8.6 g) was secured through toluene recrystallization.

$^1$H NMR (CDCl$_3$, 500 MHz) δ 7.77 (d, 2H), 7.75-7.68 (m, 2H), 7.60-7.55 (m, 1H), 7.52 (s, 1H), 7.40 (d, 2H), 7.38-7.28 (m, 5H) 7.26-7.20 (m, 2H), 7.09 (d, 2H), 6.69 (d, 2H), 4.62 (s, 1H)

[Synthesis Example 4] Synthesis of 4-(11-phenyl-11H-benzo[b]fluorene-11-yl)phenol 11H-benzo[b]fluorene-11-one (23.0 g) was added to tetrahydrofuran solvent (200 ml), and the reaction mixture was cooled to 0° C. 2M phenyl magnesium chloride tetrahydrofuran solution (60 mL) was slowly added thereto. After the addition was completed, the reaction mixture was raised to room temperature, and stirred for an additional 8 hours. After the reaction was completed, a saturated ammonium chloride aqueous solution (200 ml) was slowly added to the reaction solution, and ethyl acetate (200 ml) was added thereto, thereby performing an extraction process. A water layer was subjected to additional extraction with ethyl acetate (200 ml). Water in an oil layer was removed with anhydrous sodium sulfate, and filtered. The organic solvent was removed by distillation under reduced pressure, and high purity of 11-phenyl-11H-benzo[b]fluorene-11-ol (22.6 g) was obtained by purification using silica gel column chromatography. Phenol (68 g) and sulfuric acid (2.0 ml) were added to a dichloromethane solvent (100 ml). 11-phenyl-11H-benzo[b]fluorene-11-ol (22.6 g) was added thereto at room temperature, followed by stirring for 1 hour to perform the reaction. After the reaction, an organic layer was washed with water once and 1N sodium hydroxide aqueous solution twice. An organic solvent was removed by distillation under reduced pressure, and high purity of 4-(11-phenyl-11H-benzo[b]fluorene-11-yl)phenol (13.0 g) was secured through toluene recrystallization.

$^1$H NMR (CDCl$_3$, 500 MHz) δ 8.22 (s, 1H), 8.04-7.88 (m, 4H), 7.86 (d, 1H), 7.53-7.35 (m, 4H), 7.27 (m, 5H), 7.10 (d, 2H), 6.70 (d, 2H), 4.63 (s, 1H)

[Synthesis Example 5] Synthesis of 4-(2,7,9-triphenyl-9H-fluorene-9-yl)phenol 2,7-dibromo-9H-fluoren-9-one (24 g) was added to a solvent of toluene (800 ml) and ethanol (200 ml), and phenylboronic acid (22 g) and tetrakis(triphenylphosphine)palladium(0) (800 mg) were added thereto. 2M potassium carbonate aqueous solution (80 ml) was additionally added thereto, and the reaction mixture was raised to 80° C. and reacted for 8 hours. After the reaction was completed, the reaction mixture was cooled to room temperature, and extracted with water (1 L) and dichloromethane (2 L). Water in an oil layer was removed with anhydrous sodium sulfate, and filtered. The organic solvent was removed by distillation under reduced pressure, and high purity of 2,7-diphenyl-9H-fluorene-9-one (21.2 g) was obtained by purification using silica gel column chromatography. 2,7-diphenyl-9H-fluorene-9-one (21.2 g) was added to a tetrahydrofurane solvent (400 ml) and cooled to 0° C. 2M phenyl magnesium chloride tetrahydrofuran solution (38.4 mL) was slowly added thereto. After the addition was completed, the reaction mixture was raised to room temperature, and stirred for an additional 8 hours. After the reaction was completed, a saturated ammonium chloride aqueous solution (800 ml) was slowly added to the reaction solution, and ethyl acetate (1200 ml) was added thereto, thereby performing an extraction process. A water layer was subjected to additional extraction with ethyl acetate (600 ml). Water in an oil layer was removed with anhydrous sodium sulfate, and filtered. The organic solvent was removed by distillation under reduced pressure, and high purity of 2,7,9-triphenyl-9H-fluorene-9-ol (20.4 g) was obtained by purification using silica gel column chromatography. Phenol (48 g) and sulfuric acid (4.0 ml) were added to a dichloromethane solvent (100 ml). 2,7,9-triphenyl-9H-fluorene-9-ol (20.4 g) was added thereto at room temperature, followed by stirring for 1 hour to perform the reaction. After the reaction, an organic layer was washed with water once, and 1N sodium hydroxide aqueous solution twice. An organic solvent was removed by distillation under reduced pressure, and high purity of 4-(2,7,9-triphenyl-9H-fluorene-9-yl)phenol (14.2 g) was secured through toluene recrystallization.

$^1$H NMR (CDCl$_3$, 500 MHz) δ 7.87 (d, 2H), 7.80 (s, 2H), 7.67 (m, 6H), 7.46 (m, 4H), 7.37 (m, 2H), 7.27 (m, 5H), 7.10 (d, 2H), 6.70 (d, 2H), 4.63 (s, 1H)

[Example 1] Preparation of Polymer A

The monomer of Synthetic Example 1 (10.7 g), benzaldehyde (3.7 g), toluene sulfonic acid (0.4 g) and xylene (70.0 g) were added to a flask and heated at 150° C. and stirred. Here, water to be produced was removed, and the reaction mixture was stirred at 150° C. for 5 hours. After the reaction was completed, the reaction product was cooled, and slowly added to an excess amount of hexane to precipitate the product. The precipitated product was filtered and washed and dried in a vacuum oven, thereby obtaining a compound A (11.3 g). The compound was a polymer, and a polystyrene-conversion weight average molecular weight by gel permeation chromatography (GPC) of the polymer was 4,850.

[Example 2] Preparation of Polymer B

The monomer of Synthetic Example 2 (10.1 g), benzaldehyde (3.7 g), toluene sulfonic acid (0.4 g) and xylene (70.0 g) were added to a flask and heated at 150° C. and stirred. Here, water to be produced was removed, and the reaction mixture was stirred at 150° C. for 5 hours. After the reaction was completed, the reaction product was cooled, and slowly added to an excess amount of hexane to precipitate the product. The precipitated product was filtered and washed and dried in a vacuum oven, thereby obtaining a compound B (10.8 g). The compound was a polymer, and a polystyrene-conversion weight average molecular weight by gel permeation chromatography (GPC) of the polymer was 5,500.

[Example 3] Preparation of Polymer C

The monomer of Synthetic Example 1 (10.7 g), naphthaldehyde (6.3 g), toluene sulfonic acid (0.4 g) and xylene (70.0 g) were added to a flask and heated at 150° C. and stirred. Here, water to be produced was removed, and the reaction mixture was stirred at 150° C. for 5 hours. After the reaction was completed, the reaction product was cooled, and slowly added to an excess amount of hexane to precipitate the product. The precipitated product was filtered and washed and dried in a vacuum oven, thereby obtaining a compound C (12.9 g). The compound was a polymer, and a polystyrene-conversion weight average molecular weight by gel permeation chromatography (GPC) of the polymer was 4,450.

[Example 4] Preparation of Polymer D

The monomer of Synthetic Example 2 (10.1 g), naphthaldehyde (6.3 g), toluene sulfonic acid (0.4 g) and xylene (70.0 g) were added to a flask and heated at 150° C. and stirred. Here, water to be produced was removed, and the reaction mixture was stirred at 150° C. for 5 hours. After the reaction was completed, the reaction product was cooled, and slowly added to an excess amount of hexane to precipitate the product. The precipitated product was filtered and washed and dried in a vacuum oven, thereby obtaining a compound D (11.2 g). The compound was a polymer, and a polystyrene-conversion weight average molecular weight by gel permeation chromatography (GPC) of the polymer was 5,320.

[Example 5] Preparation of Polymer E

The monomer of Synthetic Example 3 (12.7 g), benzaldehyde (3.7 g), toluene sulfonic acid (0.4 g) and xylene (70.0 g) were added to a flask and heated at 150° C. and stirred. Here, water to be produced was removed, and the reaction mixture was stirred at 150° C. for 5 hours. After the reaction was completed, the reaction product was cooled, and slowly added to an excess amount of hexane to precipitate the product. The precipitated product was filtered and washed and dried in a vacuum oven, thereby obtaining a compound E (9.8 g). The compound was a polymer, and a polystyrene-conversion weight average molecular weight by gel permeation chromatography (GPC) of the polymer was 6,320.

[Example 6] Preparation of Polymer F

The monomer of Synthetic Example 4 (13.5 g), benzaldehyde (3.7 g), toluene sulfonic acid (0.4 g) and xylene (70.0 g) were added to a flask and heated at 150° C. and stirred. Here, water to be produced was removed, and the reaction mixture was stirred at 150° C. for 5 hours. After the reaction was completed, the reaction product was cooled, and slowly added to an excess amount of hexane to precipitate the product. The precipitated product was filtered and washed and dried in a vacuum oven, thereby obtaining a compound F (11.7 g). The compound was a polymer, and a polystyrene-conversion weight average molecular weight by gel permeation chromatography (GPC) of the polymer was 5,180.

[Example 7] Preparation of Polymer G

The monomer of Synthetic Example 5 (17.3 g), benzaldehyde (3.7 g), toluene sulfonic acid (0.4 g) and xylene (70.0 g) were added to a flask and heated at 150° C. and stirred. Here, water to be produced was removed, and the reaction mixture was stirred at 150° C. for 5 hours. After the reaction was completed, the reaction product was cooled, and slowly added to an excess amount of hexane to precipitate the product. The precipitated product was filtered and washed and dried in a vacuum oven, thereby obtaining a compound G (12.1 g). The compound was a polymer, and a polystyrene-conversion weight average molecular weight by gel permeation chromatography (GPC) of the polymer was 4,730.

[Comparative Example 1]
Preparation of Polymer H 9,9-bis(4-hydroxyphenyl)fluorene (20 g), benzaldehyde (7.3 g), toluene sulfonic acid (0.8 g) and xylene (140 g) were added to a flask and heated at 150° C. and stirred. Here, the produced water was removed, and the reaction mixture was stirred at 150° C. for 5 hours. After the reaction was completed, the reaction product was cooled, and slowly added to an excess amount of hexane to precipitate the product. The precipitated product was filtered and washed and dried in a vacuum oven, thereby obtaining a compound H (21.5 g). The compound was a polymer, and a polystyrene-conversion weight average molecular weight by gel permeation chromatography (GPC) of the polymer was 6,200.

Thermal stability of the polymer resins prepared by Examples 1 to 7 and the polymers prepared by Comparative Example 1 was measured by using a thermogravimetric analyzer (TGA, TA instruments, USA), and results thereof were shown in Table 1 below.

TABLE 1

| | Polymer | Heating temperature (° C.) | Weight loss due to TGA (wt %) |
|---|---|---|---|
| Example 1 | A | 400 | 9.01 |
| Example 2 | B | 400 | 8.25 |
| Example 3 | C | 400 | 9.29 |
| Example 4 | D | 400 | 9.24 |
| Example 5 | E | 400 | 8.58 |
| Example 6 | F | 400 | 9.05 |
| Example 7 | G | 400 | 9.04 |
| Comparative Example 1 | H | 400 | 12.55 |

[Examples 8 to 14 and Comparative Example 2]
Preparation of Resist Underlayer Film Composition According to compositions described in Table 2 below, the polymer, the crosslinking agent, and the acid catalyst were dissolved in the solvent, and filtered with a 0.05 μm filter to prepare a resist underlayer film composition of which particulate impurities were completely removed.

The polymers obtained by Examples 1 to 7 and Comparative Example 1 were used.

1,3,4,6-tetrakis(methoxymethyl)glycoluril of Chemical Formula 3-1 was used as the crosslinking agent and pyridinium p-toluenesulfonate of Chemical Formula 4-2 was used as the acid catalyst.

Propylene glycol monomethyl ether acetate (PGMEA) was used as the solvent.

TABLE 2

| | Polymer resin | Crosslinking agent | Catalyst | Solvent |
|---|---|---|---|---|
| Example 8 | 3 g (A of Example 1) | 0.15 g | 0.011 g | 30 g |
| Example 9 | 3 g (B of Example 2) | 0.15 g | 0.011 g | 30 g |
| Example 10 | 3 g (C of Example 3) | 0.15 g | 0.011 g | 30 g |
| Example 11 | 3 g (D of Example 4) | 0.15 g | 0.011 g | 30 g |
| Example 12 | 3 g (E of Example 5) | 0.15 g | 0.011 g | 30 g |
| Example 13 | 3 g (F of Example 6) | 0.15 g | 0.011 g | 30 g |
| Example 14 | 3 g (G of Example 7) | 0.15 g | 0.011 g | 30 g |
| Comparative Example 2 | 3 g (H of Comparative Example 1) | 0.15 g | 0.011 g | 30 g |

[Experimental Example 1] Formation and Evaluation of Resist Underlayer Film

The underlayer film compositions of Examples 8 to 14 and Comparative Example 2 were applied on each silicon wafer by spin-coating, followed by heating (baking) at 400° C. for 120 seconds, thereby forming a resist underlayer film having a thickness of 2800 Å.

Crosslinking degree, surface uniformity, whether crack occurs, pattern roughness, whether fume occurs (400° C.), etching resistance, and solubility were evaluated by observing a surface by the naked eyes or SEM (scanning electron microscope), etc. Results thereof were shown in Table 3 below, wherein ⊚ means significantly excellent, ○ means excellent, Δ means medium, and x means poor.

TABLE 3

| | Resist underlayer film composition | Cross linking degree | Surface uniformity | Whether crack occurs | Whether Fume occurs (400° C.) | Etching resistance | Solubility |
|---|---|---|---|---|---|---|---|
| 1 | Example 8 | ⊚ | ⊚ | none | Not occur | ○ | ⊚ |
| 2 | Example 9 | ⊚ | ⊚ | none | Not occur | ○ | ⊚ |
| 3 | Example 10 | ⊚ | ⊚ | none | Not occur | ○ | ⊚ |
| 4 | Example 11 | ⊚ | ⊚ | none | Not occur | ○ | ⊚ |
| 5 | Example 12 | ⊚ | ⊚ | none | Not occur | ⊚ | ⊚ |
| 6 | Example 13 | ⊚ | ⊚ | none | Not occur | ⊚ | ⊚ |
| 7 | Example 14 | ⊚ | ⊚ | none | Not occur | ⊚ | ⊚ |
| 8 | Comparative Example 2 | ⊚ | ○ | none | Slightly occur | ○ | ○ |

Evaluation 1: Crosslinking Degree

In order to confirm a crosslinking ability of the formed resist underlayer film, after the heating process was performed, a thickness of the underlayer film was measured, and the wafer on which the underlayer film was formed was immersed in an ethyl lactate solution for 1 minute, and washed with distilled water to completely remove ethyl lactate, followed by baking on a hot plate at 100° C. for 10 seconds. Then, a thickness of the underlayer film was measured again, thereby confirming a solubility of the resist underlayer film.

Evaluation 2: Gap-Fill Characteristic and Planarization Characteristic

The underlayer film compositions of Examples 8 to 14 and Comparative Example 2 were applied on each silicon wafer having etched patterns by spin-coating, followed by heat treatment at 400° C. for 120 seconds, thereby forming an underlayer film. Then, gap-fill characteristic and planarization characteristic were observed by using a field emission scanning electron microscope (FE-SEM). The gap-fill characteristic was evaluated by observing a cross section of the patterns by using FE-SEM, and confirming whether void occurs, and the planarization characteristic was evaluated by measuring thicknesses of the underlayer film from an image of the cross section of the patterns observed by using FE-SEM and calculating according to the following calculation formula 1. Since the planarization characteristic is excellent when a difference between h1 and h2 is not large, the planarization characteristic is more excellent as the numerical value becomes smaller. Results of the gap-fill characteristic and planarization characteristic were shown in Table 4 below, wherein ⊚ means significantly excellent, ○ means excellent, Δ means medium, and x means poor.

[Calculation Formula 1]

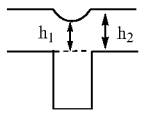

$$\text{Planarization} = \left(1 - \frac{h_2}{h_1}\right) \times 100$$

TABLE 4

| Resist underlayer film composition | Planarization characteristic | Gap-fill characteristic |
|---|---|---|
| Example 8 | ⊚ | ⊚ |
| Example 9 | ⊚ | ⊚ |
| Example 10 | ⊚ | ⊚ |
| Example 11 | ⊚ | ⊚ |
| Example 12 | ○ | ○ |
| Example 13 | ○ | ○ |
| Example 14 | ○ | ○ |
| Comparative Example 2 | ○ | ○ |

Evaluation 3: Thermal Stability

The resist underlayer film compositions of Examples 8 to 14 and Comparative Example 2 were applied on each silicon wafer by spin-on coating, followed by heat treatment on a hot plate at 240° C. for 1 minute, thereby forming a thin film. A thickness of the formed thin film was measured by a thin film thickness measurement system (K-MAC Co., Ltd). Next, the thin film was subjected to heat treatment at 400° C. for 2 minutes again, and a thickness of the thin film was measured. Meanwhile, whether fume occurs at the time of heat treatment at 240° C. and 400° C. was observed with the naked eye. Results of the reduction degree in thin film thickness and whether fume occurs were shown in Table 5 below.

TABLE 5

| Resist underlayer film composition | Reduction degree in thin film thickness | Whether fume occurs |
|---|---|---|
| Example 8 | Not almost reduced | Not occur |
| Example 9 | Not almost reduced | Not occur |
| Example 10 | Not almost reduced | Not occur |
| Example 11 | Not almost reduced | Not occur |
| Example 12 | Not almost reduced | Not occur |
| Example 13 | Not almost reduced | Not occur |
| Example 14 | Not almost reduced | Not occur |
| Comparative Example 2 | Slightly reduced | Slightly occur |

Evaluation 4: Etching Resistance

The resist underlayer film compositions of Examples 8 to 14 and Comparative Example 2 were applied on each silicon wafer by spin-on coating, followed by heat treatment (baking) on a hot plate at 400° C. for 2 minutes, thereby forming an underlayer film. Then, a thickness of the underlayer film was measured. Next, the underlayer film was subjected to dry-etching for 60 seconds and 100 seconds, respectively using $N_2/O_2$ mixed gas and $CF_x$ gas, and a thickness of the underlayer film was measured again. A bulk etch rate (BER) was calculated by using the thicknesses of the underlayer film before and after dry-etching and etching time according to the following Calculation Formula 2.

(Thickness of initial thin film−Thickness of thin film after etching)/Etching time (Å/s)   [Calculation Formula 2]

TABLE 6

| Resist underlayer film composition | $N_2/O_2$ bulk Etch rate (Å/s) | $CF_x$ bulk etch rate (Å/s) |
|---|---|---|
| Example 8 | 25 | 23 |
| Example 9 | 24 | 23 |
| Example 10 | 24.5 | 22 |
| Example 11 | 23.5 | 23 |
| Example 12 | 22 | 21.5 |
| Example 13 | 22.5 | 21 |
| Example 14 | 21.5 | 21 |
| Comparative Example 2 | 26 | 25 |

Evaluation 5: Solubility and Storage Stability

Each of the following solvents for test was mixed with PGMEA 20% solution at a ratio of 1:1. Then, whether a precipitate occurs over time and a change with the passage of time were tracked and evaluated at 50° C. for 21 days. Results of the solubility and storage stability were shown in Table 7 below, wherein ⊚ means significantly excellent, ○ means excellent, Δ means medium, and x means poor.

Solvents for Test: E/L (Ethyl lactate), PGME, C/H(Cyclohexanone), PGME/PGMEA: 70/30 or EEP (Ethyl 3-ethoxy propionate)

TABLE 7

| Resist underlayer film composition | Solubility | Storage stability |
|---|---|---|
| Example 8 | ⊚ | ⊚ |
| Example 9 | ⊚ | ⊚ |
| Example 10 | ⊚ | ⊚ |
| Example 11 | ⊚ | ⊚ |
| Example 12 | ⊚ | ⊚ |
| Example 13 | ⊚ | ⊚ |
| Example 14 | ⊚ | ⊚ |
| Comparative Example 2 | ○ | ○ |

Evaluation 6: Formation of Patterns

Figure 2:
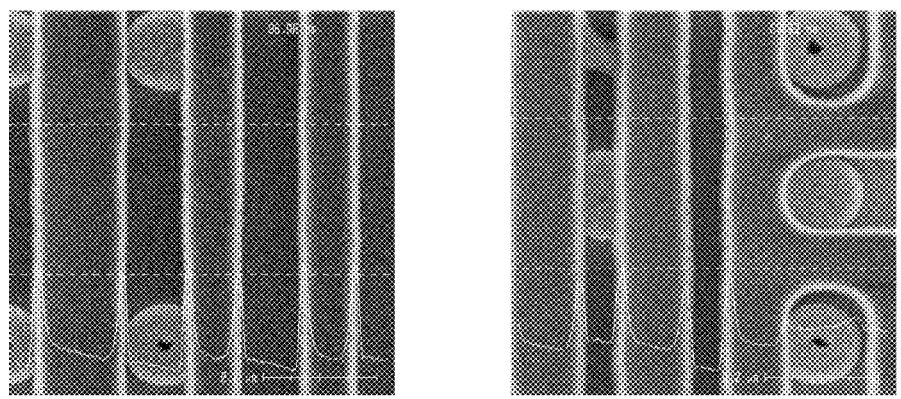
FIG. 2 shows CD point images after an etching process in evaluation 6 of Experimental Example 1.

A thin film having a thickness of 2800 Å was formed on a silicon wafer by using the underlayer film composition of Example 9 through the spin-on coating method of Experimental Example 1, and a SiON layer was formed on the thin film by chemical vapor deposition (CVD). Then, an anti-reflective coating film (organic BARC) was spin-coated thereon at a thickness of 230 Å and cured by heat treatment (baking) at 240° C. for 60 seconds. Then, a patterning process was performed on the film by using a photoresist. Next, the SiON layer was etched with fluorine base ($CF_4$) and $O_2/N_2$ base gas by using the photoresist as a protective layer, and the SOC (spin on carbon) layer was etched by using the etched SiON layer as the protective layer. Results thereof were shown in FIGS. 1 and 2.

Since the novel polymer for preparing a resist underlayer film according to the present invention simultaneously has excellent thermal stability, etching resistance, and planarization characteristic, the resist underlayer film composition containing the polymer may form a spin on carbon (SOC) hard mask by spin-coating in a multilayer semiconductor lithography process. Further, fume may less occur in a post process heated at 400° C., such that the resist underlayer film composition containing the polymer is useful as a high-temperature SOC material.

The resist underlayer film composition containing the polymer of the present invention may have excellent etching resistance, thermal stability, and coating uniformity, and particularly, may have excellent solubility to organic solvents even though the polymer has a high carbon content, thereby remarkably improving storage stability and line compatibility in a semiconductor process.

In addition, the resist underlayer film formed according to the present invention may have excellent thermal stability and excellent gap-fill characteristic even when being applied on the wafer having steps, thereby achieving excellent planarization. Further, the resist underlayer film formed according to the present invention may have excellent etching resistance to thereby serve as a protective layer (hard mask) for forming shapes of predetermined patterns at the time of a dry etching process, to minimize a loss of the mask as the etching speed of the resist film becomes fast or slow, and to increase an etching amount of the substrate.

In addition, even in the case in which the resist underlayer film formed by using the resist underlayer film composition of the present invention is subjected to a photolithography process and an etching process, the resist underlayer film has excellent results in view of pattern fidelity, CD (critical dimension) uniformity, surface roughness, etc.

What is claimed is:

1. A polymer for preparing a resist underlayer film comprising:
a repeating unit represented by Chemical Formula 1-2, 1-3, 1-4, 1-5, 1-6, 1-7, 1-8, 1-9, 1-11, 1-15, 1-16, 1-17, 1-18, 1-19, 1-20, 1-21, 1-22, 1-23, 1-24, 1-25 or 1-26 below:

[Chemical Formula 1-2]

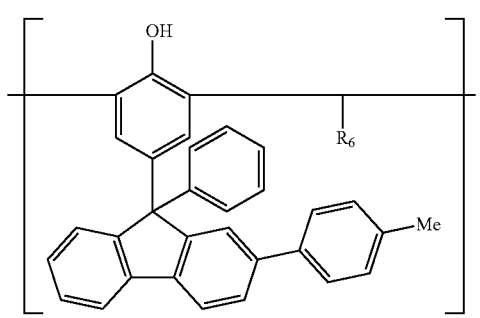

[Chemical Formula 1-3]
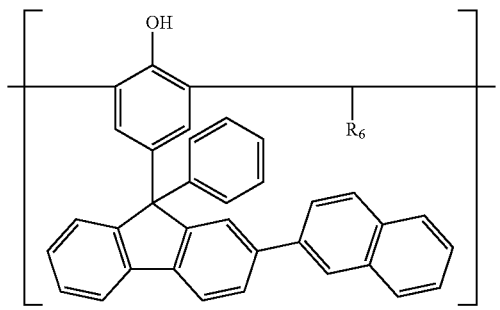
[Chemical Formula 1-4]
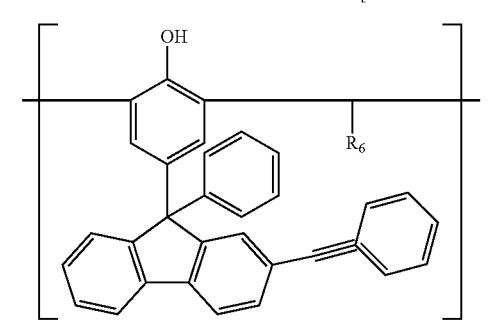
[Chemical Formula 1-5]
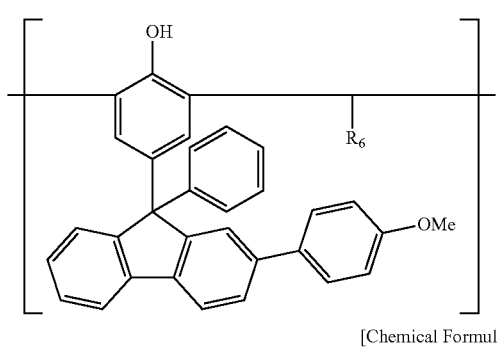
[Chemical Formula 1-6]
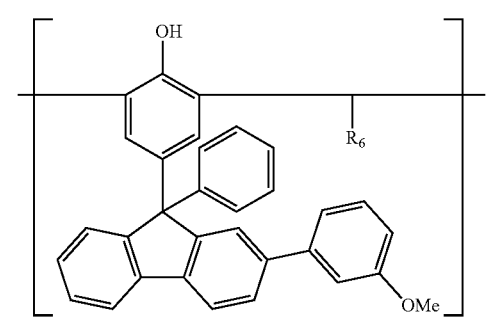
[Chemical Formula 1-7]
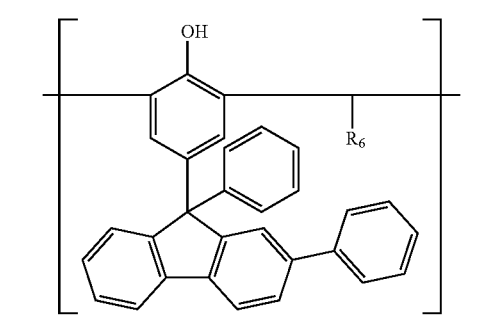
[Chemical Formula 1-8]
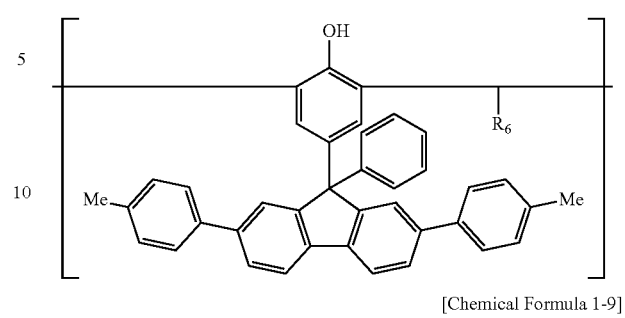
[Chemical Formula 1-9]
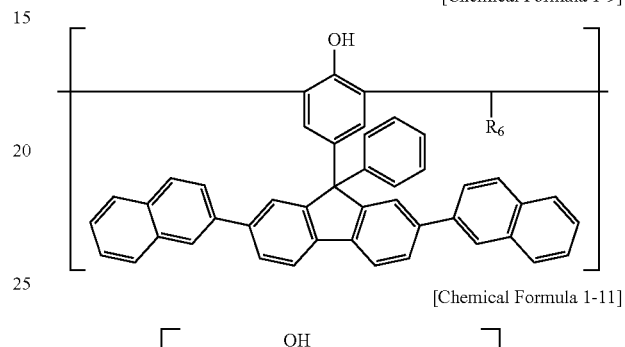
[Chemical Formula 1-11]
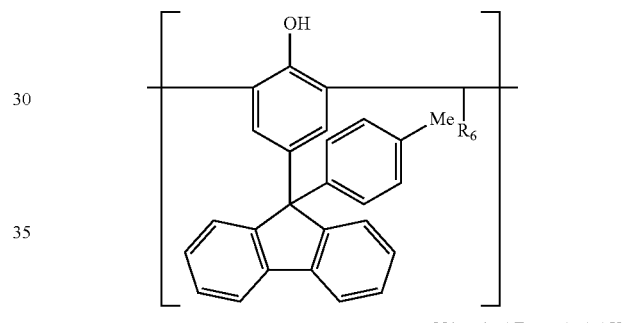
[Chemical Formula 1-15]
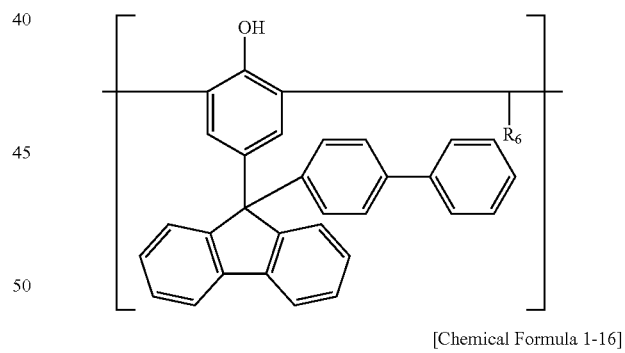
[Chemical Formula 1-16]
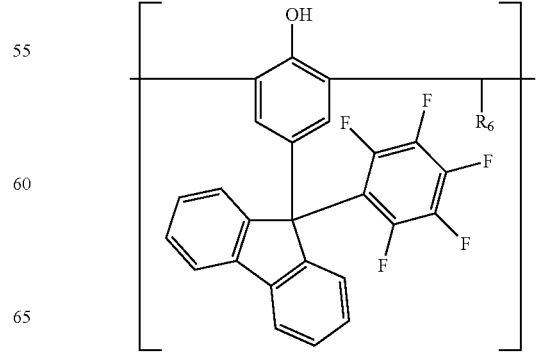

[Chemical Formula 1-17]
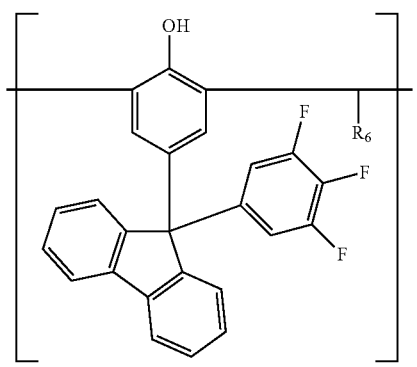
[Chemical Formula 1-18]
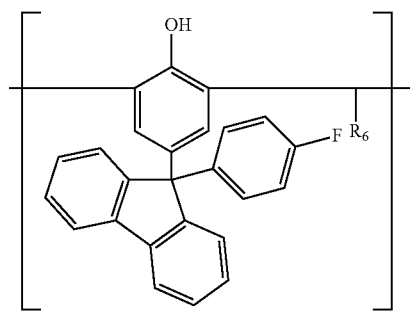
[Chemical Formula 1-19]
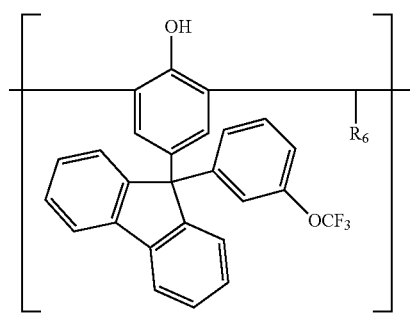
[Chemical Formula 1-20]
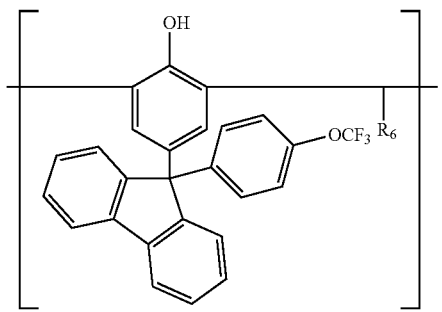
[Chemical Formula 1-21]
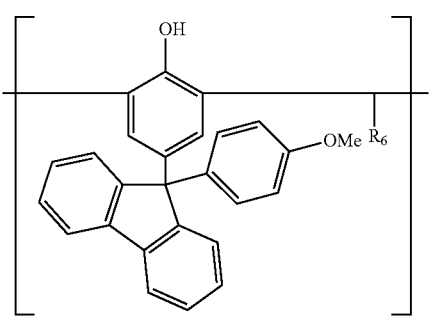
[Chemical Formula 1-22]
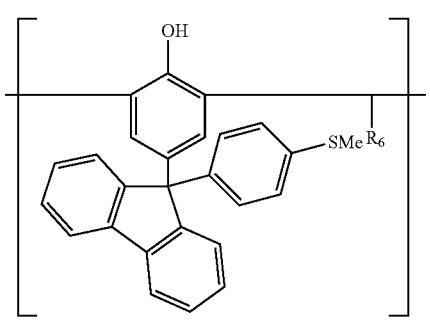
[Chemical Formula 1-23]
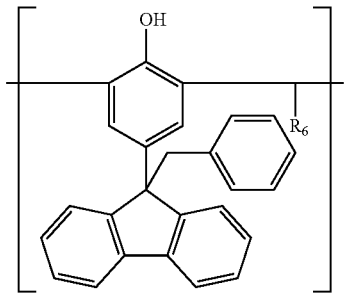
[Chemical Formula 1-24]
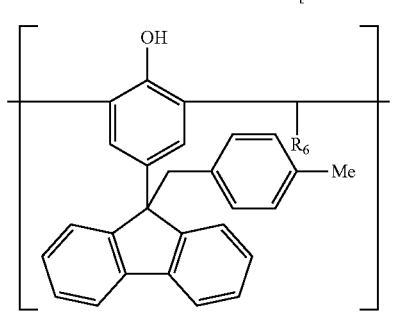

-continued

[Chemical Formula 1-25]

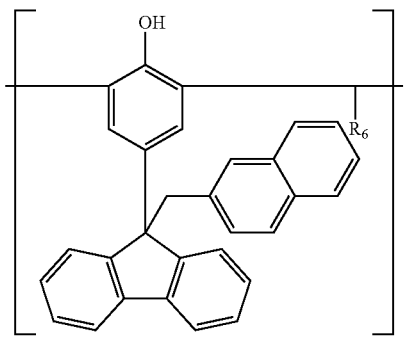

[Chemical Formula 1-26]

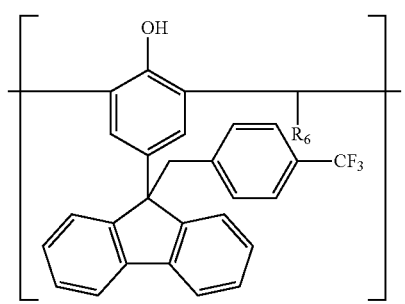

R$_6$ is hydrogen, (C1-C10)alkyl, (C3-C10)cycloalkyl or (C6-C20)aryl, and the alkyl, cycloalkyl, or aryl of R$_6$ may be further substituted with one or more substituents selected from the group consisting of (C1-C10) alkyl and (C6-C20)aryl.

2. The polymer for preparing a resist underlayer film of claim 1, further comprising: a repeating unit represented by Chemical Formula 3 below:

[Chemical Formula 3]

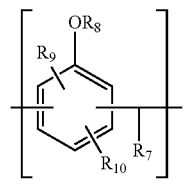

in Chemical Formula 3, R$_7$ is hydrogen, (C1-C10)alkyl, (C3-C10)cycloalkyl or (C6-C20)aryl, and the alkyl, cycloalkyl, or aryl of R$_7$ may be further substituted with one or more substituents selected from the group consisting of (C1-C10)alkyl and (C6-C20)aryl;

R$_8$ is hydrogen, (C1-C10)alkyl, (C3-C10)cycloalkyl, (C6-C20)aryl, (C1-C10)alkyl(C6-C20)aryl or (C6-C20)aryl(C1-C10)alkyl; and R$_9$ and R$_{10}$ are each independently hydrogen, (C1-C10)alkyl, (C3-C10)cycloalkyl, (C6-C20)aryl, (C1-C10)alkoxy, (C6-C20)aryloxy, (C1-C10)alkyl(C6-C20)aryl or (C6-C20)aryl(C1-C10)alkyl.

3. The polymer for preparing a resist underlayer film of claim 1, wherein the polymer for preparing a resist underlayer film has a weight average molecular weight of 500 or more.

4. The polymer for preparing a resist underlayer film of claim 3, wherein the polymer for preparing a resist underlayer film has a weight average molecular weight of 500 to 20,000.

5. A resist underlayer film composition comprising:
a polymer for preparing a resist underlayer film including a repeating unit represented by Chemical Formula 1-2, 1-3, 1-4, 1-5, 1-6, 1-7, 1-8, 1-9, 1-11, 1-15, 1-16, 1-17, 1-18, 1-19, 1-20, 1-21, 1-22, 1-23, 1-24, 1-25 or 1-26 below; and
an organic solvent:

[Chemical Formula 1-2]

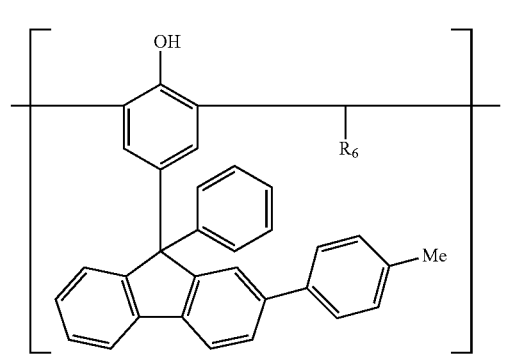

[Chemical Formula 1-3]

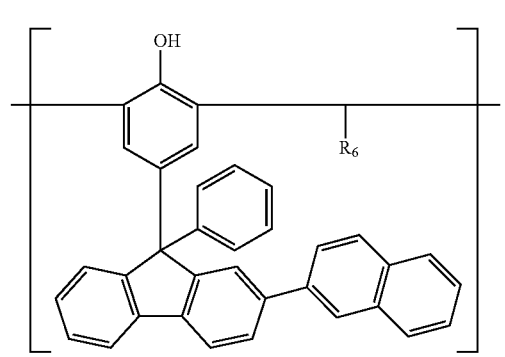

[Chemical Formula 1-4]
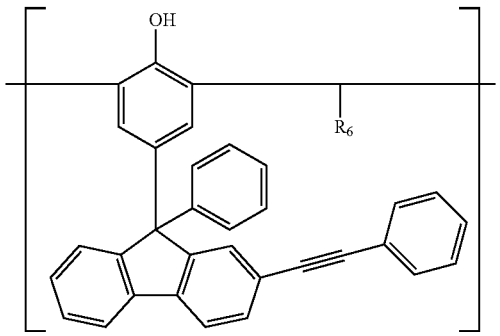
[Chemical Formula 1-5]
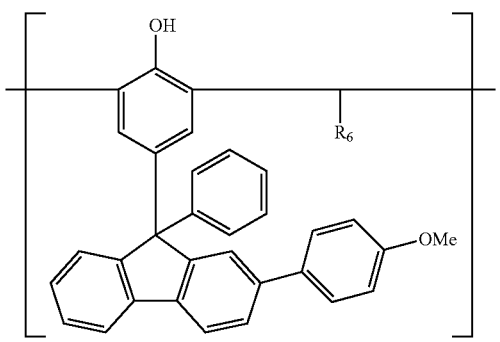
[Chemical Formula 1-6]
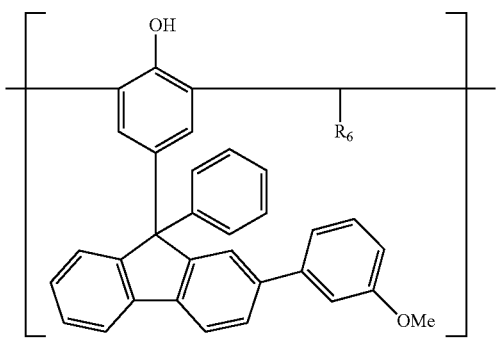
[Chemical Formula 1-7]
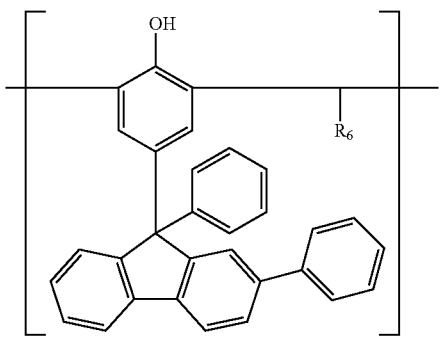

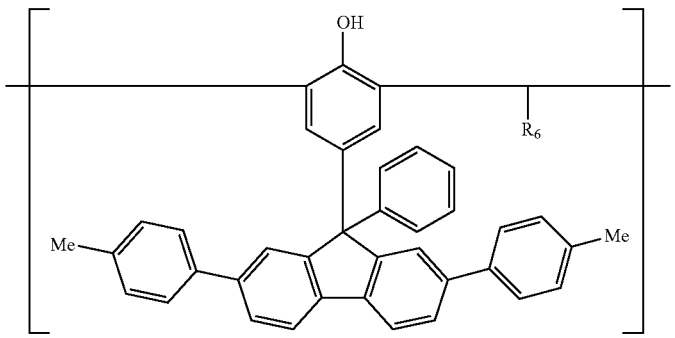
[Chemical Formula 1-8]
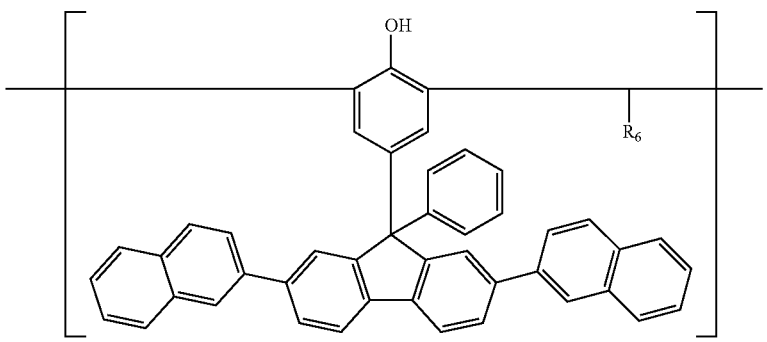
[Chemical Formula 1-9]
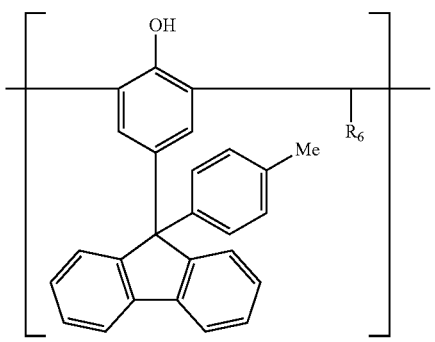
[Chemical Formula 1-11]
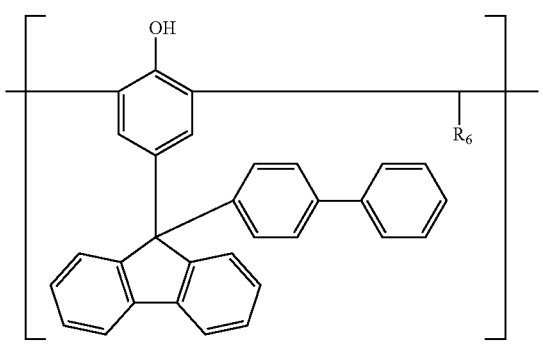
[Chemical Formula 1-15]

[Chemical Formula 1-16]
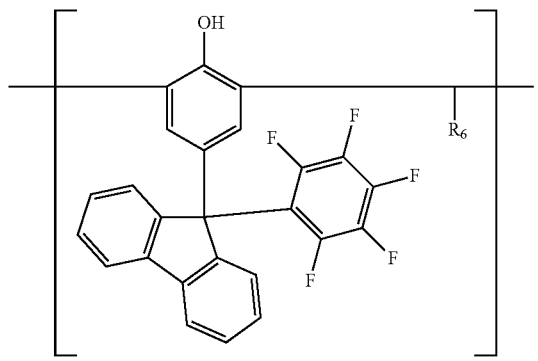
[Chemical Formula 1-17]
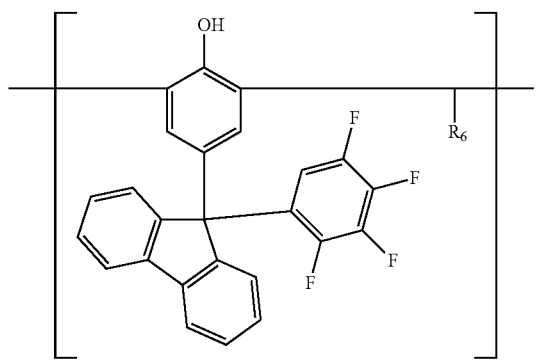
[Chemical Formula 1-18]
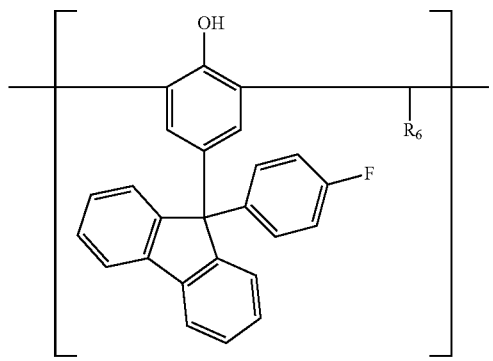
[Chemical Formula 1-19]
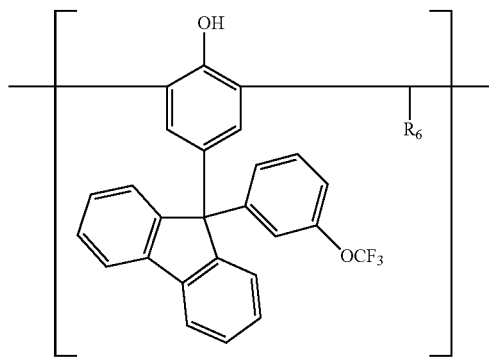

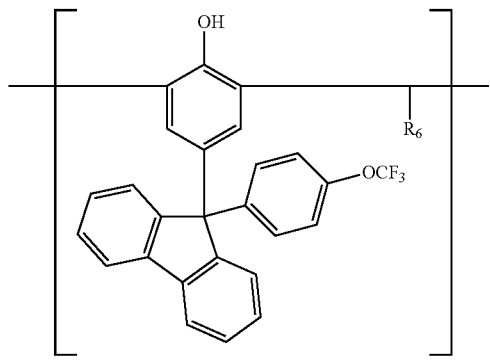
[Chemical Formula 1-20]
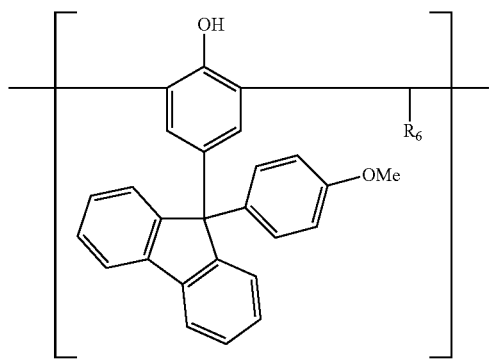
[Chemical Formula 1-21]
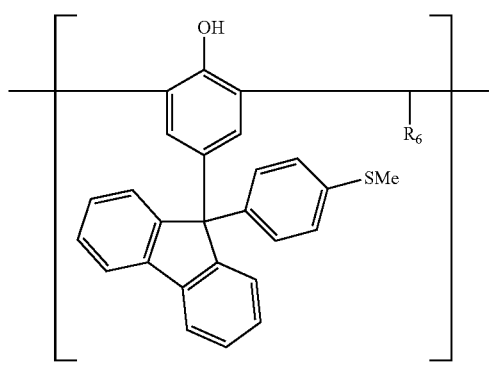
[Chemical Formula 1-22]
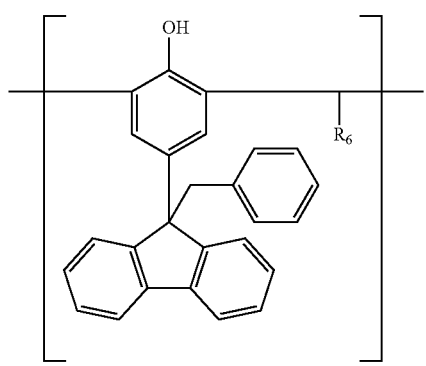
[Chemical Formula 1-23]

-continued

[Chemical Formula 1-24]

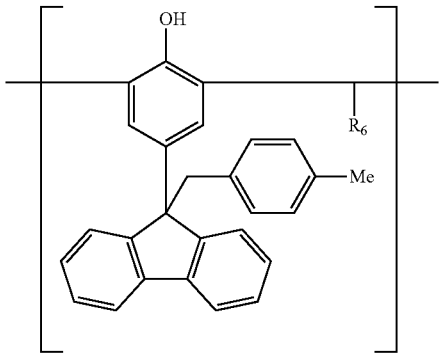

[Chemical Formula 1-25]

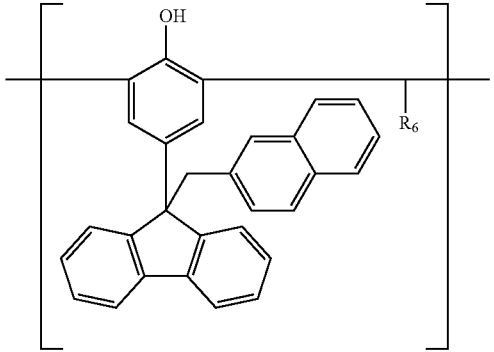

[Chemical Formula 1-26]

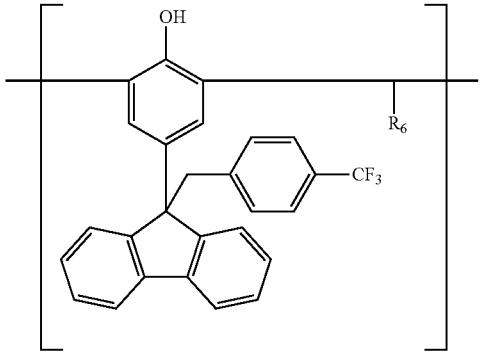

$R_6$ is hydrogen, (C1-C10)alkyl, (C3-C10)cycloalkyl or (C6-C20)aryl, and the alkyl, cycloalkyl, or aryl of $R_6$ may be further substituted with one or more substituents selected from the group consisting of (C1-C10) alkyl and (C6-C20)aryl.

6. The resist underlayer film composition of claim 5, wherein the polymer for preparing a resist underlayer film further includes a repeating unit represented by Chemical Formula 3 below:

[Chemical Formula 3]

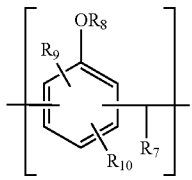

in Chemical Formula 3, $R_7$ is hydrogen, (C1-C10)alkyl, (C3-C10)cycloalkyl or (C6-C20)aryl, and the alkyl, cycloalkyl, or aryl of $R_7$ may be further substituted with one or more substituents selected from the group consisting of (C1-C10)alkyl and (C6-C20)aryl;

$R_8$ is hydrogen, (C1-C10)alkyl, (C3-C10)cycloalkyl, (C6-C20)aryl, (C1-C10)alkyl(C6-C20)aryl or (C6-C20)aryl(C1-C10)alkyl; and $R_9$ and $R_{10}$ are each independently hydrogen, (C1-C10)alkyl, (C3-C10)cycloalkyl, (C6-C20)aryl, (C1-C10)alkoxy, (C6-C20)aryloxy, (C1-C10)alkyl(C6-C20)aryl or (C6-C20)aryl(C1-C10)alkyl.

7. The resist underlayer film composition of claim 5, wherein the composition comprises the polymer for preparing a resist underlayer film in an amount of 0.5 to 50 wt % and the organic solvent in an amount of 50 to 99.5 wt %, based on total amount of the resist underlayer film composition.

8. The resist underlayer film composition of claim 7, wherein the organic solvent is at least one selected from cyclohexanone, 2-heptanone, propyleneglycol monomethyl ether, propyleneglycol monomethyl acetate, propyleneglycol monomethyl ether acetate, gamma-butyrolactone, ethyl lactate, dimethyl sulfoxide, dimethyl acetamide, and N-methyl pyrrolidone.

9. The resist underlayer film composition of claim 5, further comprising at least one additive selected from the group consisting of a crosslinking agent, an acid catalyst, an acid generator, an antifoaming agent, and a surfactant.

10. The resist underlayer film composition of claim 9, wherein the crosslinking agent is at least one selected from the group consisting of a compound represented by Chemical Formula 4-1, a compound represented by Chemical Formula 4-2, a compound represented by Chemical Formula 4-3, a compound represented by Chemical Formula 4-4, a compound represented by Chemical Formula 4-5, a compound represented by Chemical Formula 4-6, and a compound represented by Chemical Formula 4-7 below:

[Chemical Formula 4-1]

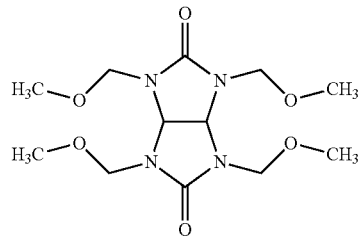

[Chemical Formula 4-2]

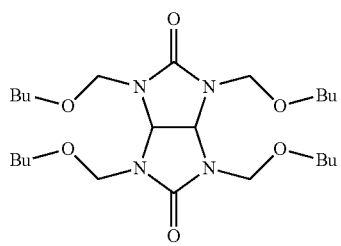

[Chemical Formula 4-3]

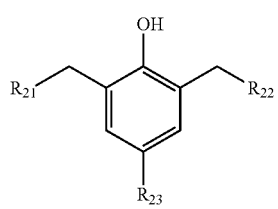

in Chemical Formula 4-3, $R_{21}$ and $R_{22}$ are each independently hydroxy or (C1-C3)alkoxy, and $R_{23}$ is (C1-C10)alkyl,

[Chemical Formula 4-4]

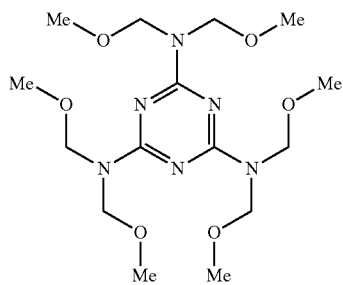

[Chemical Formula 4-5]

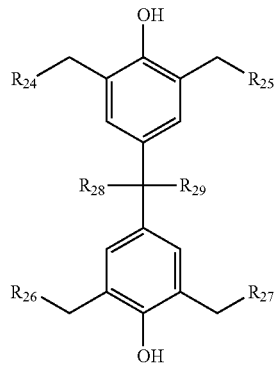

in Chemical Formula 4-5, $R_{24}$, $R_{25}$, $R_{26}$ and $R_{27}$ are each independently hydroxy or (C1-C3)alkoxy, and $R_{28}$ and $R_{29}$ are each independently hydrogen, (C1-C10)alkyl or halo(C1-C10)alkyl,

[Chemical Formula 4-6]

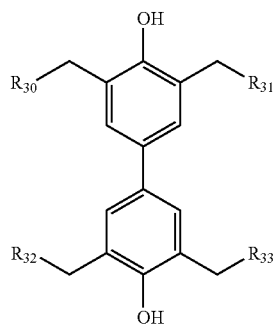

in Chemical Formula 4-6, $R_{30}$, $R_{31}$, $R_{32}$ and $R_{33}$ are each independently hydroxy or (C1-C3)alkoxy, and

[Chemical Formula 4-7]

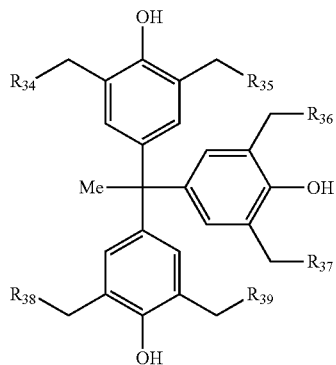

in Chemical Formula 4-7, $R_{34}$, $R_{35}$, $R_{36}$, $R_{37}$, $R_{38}$ and $R_{39}$ are each independently hydroxy or (C1-C3)alkoxy.

11. The resist underlayer film composition of claim 9, wherein the acid catalyst or the acid generator is at least one selected from the group consisting of a compound represented by Chemical Formula 5-1, a compound represented by Chemical Formula 5-2, a compound represented by Chemical Formula 5-3, a compound represented by Chemical Formula 5-4, a compound represented by Chemical Formula 5-5, and a compound represented by Chemical Formula 5-6 below:

[Chemical Formula 5-1]

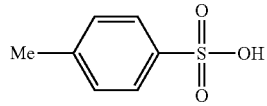

[Chemical Formula 5-2]

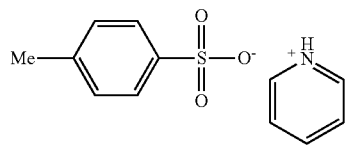

[Chemical Formula 5-3]

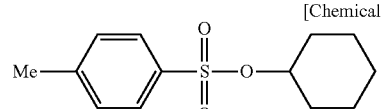

[Chemical Formula 5-4]

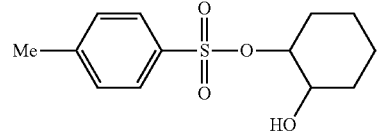

[Chemical Formula 5-5]

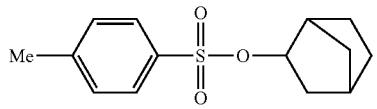

[Chemical Formula 5-6]

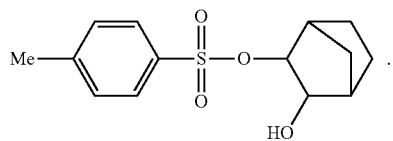

12. A method for forming a resist underlayer film comprising:
    forming a coating layer by spin-coating the resist underlayer film composition of claim 5 on a wafer; and
    forming a resist underlayer film by heating the wafer on which the coating layer is formed.

13. The method of claim 12, wherein the wafer on which the coating layer is formed is heated at 200° C. to 450° C.

* * * * *

UNITED STATES PATENT AND TRADEMARK OFFICE
CERTIFICATE OF CORRECTION

PATENT NO. : 9,695,279 B2
APPLICATION NO. : 15/133808
DATED : July 4, 2017
INVENTOR(S) : Kwang Kuk Lee et al.

Page 1 of 1

It is certified that error appears in the above-identified patent and that said Letters Patent is hereby corrected as shown below:

In the Claims

Column 41, Lines 16-28, Claim 1, delete:

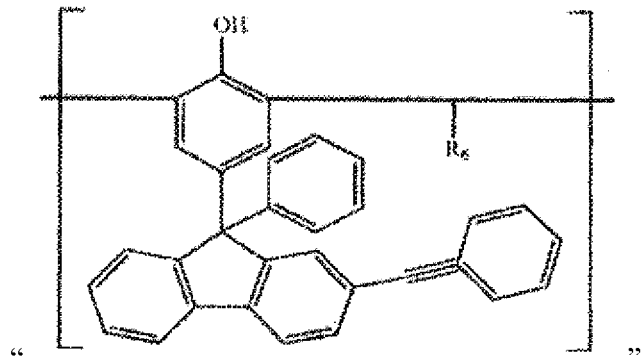

And insert:

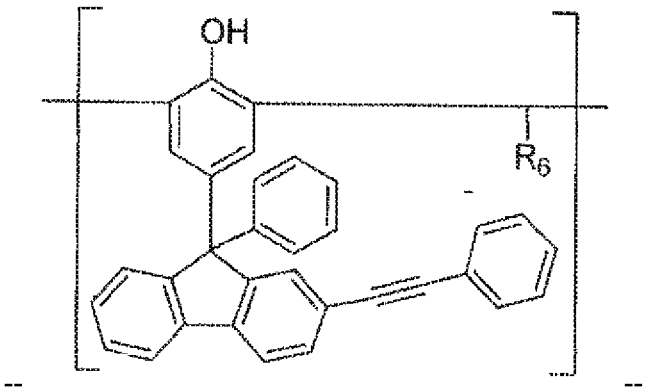

Signed and Sealed this
Seventh Day of November, 2017

Joseph Matal
*Performing the Functions and Duties of the
Under Secretary of Commerce for Intellectual Property and
Director of the United States Patent and Trademark Office*